United States Patent
Reb

(10) Patent No.: US 10,376,469 B2
(45) Date of Patent: Aug. 13, 2019

(54) MICROSPHERES CONTAINING THERAPEUTIC AGENTS AND RELATED METHODS OF USE

(71) Applicant: Biosphere Medical, Inc., South Jordan, UT (US)

(72) Inventor: Philippe Reb, Themericourt (FR)

(73) Assignee: Biosphere Medical, Inc., South Jordan, UT (US)

( * ) Notice: Subject to any disclaimer, the term of this patent is extended or adjusted under 35 U.S.C. 154(b) by 20 days.

(21) Appl. No.: 15/436,451

(22) Filed: Feb. 17, 2017

(65) Prior Publication Data

US 2017/0231915 A1 Aug. 17, 2017

Related U.S. Application Data

(60) Provisional application No. 62/296,430, filed on Feb. 17, 2016.

(51) Int. Cl.
| | |
|---|---|
| *A61K 9/16* | (2006.01) |
| *A61K 31/282* | (2006.01) |
| *A61K 31/555* | (2006.01) |
| *A61K 33/24* | (2019.01) |
| *C08F 290/10* | (2006.01) |

(52) U.S. Cl.
CPC ......... *A61K 9/1652* (2013.01); *A61K 9/1635* (2013.01); *A61K 9/1694* (2013.01); *A61K 31/282* (2013.01); *A61K 31/555* (2013.01); *A61K 33/24* (2013.01); *C08F 290/10* (2013.01)

(58) Field of Classification Search
CPC .. A61K 9/1652; A61K 9/1635; A61K 9/1682; A61K 9/1694
See application file for complete search history.

(56) References Cited

U.S. PATENT DOCUMENTS

| | | |
|---|---|---|
| 2009/0053318 A1 | 2/2009 | Tan et al. |
| 2011/0104052 A1 | 5/2011 | Barnett et al. |
| 2012/0230937 A1 | 9/2012 | Moine et al. |
| 2012/0302505 A1 | 11/2012 | Fetzer et al. |

FOREIGN PATENT DOCUMENTS

| | | | |
|---|---|---|---|
| CN | 102964538 A | * | 12/2012 |
| CN | 104922688 | | 9/2015 |
| WO | 2012120138 | | 9/2012 |

OTHER PUBLICATIONS

Bibby et al. Preparation and characterization of beta-cyclodextrin and poly(acrylic acid) microspheres.(J. Microencapsulation 1998). vol. 15, No. 5, pp. 629-637.*
International Search Report and Written Opinion dated May 22, 2017 for PCT/US2017/018496.
Anconi, et al.,Inclusion Complexes of a-Cyclodextrin and the Cisplatin Analogues Oxaliplatin, Carboplatin and Nedaplatin: A Theoretical Approach, Elsevier, Chemical Physics Letters, 515 ,2011 ,127-131.
Balaji, et al.,Synthesis and Characterization Studies of Cisplatin/Hydroxypropyl-β-Cyclodextrin Complex, Pharmaclolgyonline1 ,2009 ,1135-1143.
Bistri, et al.,Chemical Clockwise Tridifferentiation of α- and β-Cyclodextrins: Bascule-Bridge or Deoxy-Sugars Strategies, Chem. Eur. J., 13 ,2007 ,9757-9774.
Chen, et al.,Cyclodextrin-Based Inclusion Complexation Bridging Supramolecular Chemistry and Macromolecular Self-Assembly, Chem. Soc. Rev.,40 ,2011 ,2254-2266.
Chiu, et al.,Eftcient Monomodification of the Secondary Hydroxy Groups of β-Cyclodextrin, J. Org. Chem., 54 ,1999 ,332-333.
Del Valle, et al.,Cyclodextrins and Their Uses: A Review, Process Biochemistry, Department of Chemical Engineering, University of Salamanca, Spain, 39 ,2004 ,1033-1046.
D'Souza, et al.,Cyclodextrins: Introduction, American Chemical Society, Chemical Reviews, vol. 98, No. 5 ,Jul./Aug. 1998.
Ferruti, et al.,Synthesis, Characterisation and Antitumour Activity of Platinum (II) complexes of Novel Functionalised Poly(amido amine)s, Macromol. Chem. Phys., 200 ,1999 ,1644-1654.
Horvath, et al.,Supramolecular Nanoencapsulation as a Tool: Solubilization of the Anticancer Drug trans-Dichloro (dipyridine)platinum(II) by Complexation with β-Cyclodextrin, Molecular Pharmaceutics, vol. 5 No. 2,2008 ,358-363.
Rasheed, et al.,Cyclodextrins as Drug Carrier Molecule: A Review, Sci Pahrm, 76 ,2008 ,567-598.
Yao, et al.,Platinum-Incorporating Poly(N-vinypyrrolidone)-Poly(aspartic acid) Pseudoblock Copolymer Nanoparticles for Drug Delivery, Biomacromolecules, 16 ,2015 ,2059-2071.
Zhou, et al.,Cyclodextrin Functionalized Polymers as Drug Delivery Systems, Polym. Chem., 1 ,2010 ,1552-1559.

* cited by examiner

*Primary Examiner* — Lakshmi S Channavajjala
(74) *Attorney, Agent, or Firm* — Stoel Rives LLP

(57) ABSTRACT

Microspheres, compositions including the microspheres, and methods of using the microspheres are disclosed herein. The microspheres can be substantially spherical and can include a copolymer of a monomer (such as an acrylic monomer) and a cyclodextrin or a derivative thereof. The microspheres can also include a therapeutic agent, such as a platinum-based drug.

19 Claims, No Drawings

MICROSPHERES CONTAINING THERAPEUTIC AGENTS AND RELATED METHODS OF USE

RELATED APPLICATIONS

This application claims the benefit of U.S. Provisional Application No. 62/296,430, filed on Feb. 17, 2016 and titled "MICROSPHERES CONTAINING THERAPEUTIC AGENTS AND RELATED METHODS OF USE," which is hereby incorporated by reference in its entirety.

TECHNICAL FIELD

The present disclosure relates to microspheres containing therapeutic agents, to compositions including the microspheres, and to methods for preparing and using such microspheres and compositions. The microspheres and compositions can be used in the management or treatment of various diseases and disorders including cancer and other angiogenic-dependent diseases by drug delivery and/or therapeutic embolization.

DETAILED DESCRIPTION

The present disclosure relates to microspheres containing therapeutic agents, to compositions including the microspheres, and to methods for preparing and using such microspheres and compositions. The microspheres and compositions can be used in the management or treatment of various diseases and disorders including cancer and other angiogenic-dependent diseases by drug delivery and/or therapeutic embolization.

It will be readily understood that the embodiments, as generally described herein, are exemplary. The following detailed description of various embodiments is not intended to limit the scope of the present disclosure, but is merely representative of various embodiments. It will be appreciated that various features are sometimes grouped together in a single embodiment or description thereof for the purpose of streamlining the disclosure. Many of these features may be used alone and/or in combination with one another. Moreover, the order of the steps or actions of the methods disclosed herein may be changed by those skilled in the art without departing from the scope of the present disclosure. In other words, unless a specific order of steps or actions is required for proper operation of the embodiments, the order or use of specific steps or actions may be modified.

Definitions

As used herein, the term "about" means within 20%, within 15%, within 10%, within 5%, or within 1% or less of a given value or range. Further, all ranges include both endpoints.

As used herein, "administered," "administering," or "administration" refers to the act of injecting or otherwise physically delivering a substance as it exists outside the body (e.g., a microsphere or composition) into a patient, such as by, but not limited to, pulmonary (e.g., inhalation), mucosal (e.g., intranasal), intradermal, intravenous, intramuscular delivery, and/or any other method of physical delivery described herein or known in the art. When a disease, or symptoms thereof, is being managed or treated, administration of the therapy (such as the microspheres disclosed herein) typically occurs after the onset of the disease or symptoms thereof. When a disease, or symptoms thereof, is being prevented, administration of the therapy (such as the microspheres disclosed herein) typically occurs before the onset of the disease or symptoms thereof.

As used herein, "cell adhesion promoter" means any material that, because of its presence in or association with the microspheres, promotes or enhances the adhesiveness of cells to the surface of the microspheres. These materials can include proteins that are associated with the surface of the microspheres through covalent bonds or in an interpenetrated polymeric manner.

As used herein, the term "effective amount" refers to the amount of a therapy (e.g., a microsphere or composition disclosed herein) which is sufficient to reduce and/or ameliorate the severity and/or duration of a given disease and/or a symptom related thereto.

As used herein, "elastic" microspheres refer to microspheres that comprise polymers that have elastic properties.

As used herein, "hydrophilic" refers to microspheres or portions of microspheres which may substantially bind with, absorb, mix easily with, and/or dissolve in water or aqueous solutions. This may result in swelling and/or the formation of reversible gels.

As used herein, "injectable" means capable of being administered, delivered, or carried into the body via syringe, catheters, needles, or other means for injecting or infusing the microspheres in a liquid medium.

As used herein, the terms "manage," "manacling," and "management" refer to the beneficial effects that a subject derives from a therapy (e.g., the microspheres disclosed herein), which does not result in a cure of the infection. In certain embodiments, a subject is administered one or more therapies to "manage" a given disease or one or more symptoms related thereto, so as to prevent the progression or worsening of the disease.

As used herein, "microspheres" means polymer or combinations of polymers made into bodies of various sizes. The microspheres can be in any shape, although they are often substantially spherical. In certain embodiments, the microspheres are sterile, either alone or when in the form of a pharmaceutical composition. The microspheres and compositions may be sterilized by any method known in the art, for example, by irradiation, such as gamma or beta irradiation. The microspheres may comprise other materials as described and defined herein.

As used herein, "monomer composition" means any composition comprising at least one monomer that may be polymerized to form a polymer or copolymer. The monomer composition may optionally comprise other components besides the at least one monomer. For example, the monomer composition may comprise additional agents to aid in the polymerization process, or it may comprise non-monomer compositions or components that can be incorporated or associated with the final polymer or copolymer after polymerization. In the context of a polymer or copolymer, a polymer or copolymer comprises a monomer if the polymer or copolymer has at least one of the monomer covalently bound to the polymer or copolymer (e.g., a polymerized monomer.)

The term "pharmaceutically acceptable" as used herein means being approved by a regulatory agency of the federal or a state government, or listed in the U.S. Pharmacopeia, European Pharmacopeia, or other generally recognized pharmacopeia for use in animals, and more particularly in humans.

As used herein, "polymerize" or "polymerizing" means any action taken to cause one or more monomers to become covalently bound to form a polymer or copolymer. For example, a monomer composition or mixture may be polymerized by adding an activating agent to the monomer composition or mixture to induce formation of a polymer or copolymer. In some embodiments, the activating agent comprises N,N,N',N'-tetramethylethylenediamine.

As used herein, the term "prevent" refers to the total or partial inhibition of a given disease; the total or partial inhibition of the development or onset of disease progression of given disease, or a symptom related thereto in a subject; or the total or partial inhibition of the progression of a given disease or a symptom related thereto.

As used herein, "substantially spherical" generally means a shape that is close to a perfect sphere, which is defined as a volume that presents the lowest external surface area. For example, "substantially spherical" can refer to microspheres wherein, when viewing any cross-section of the microspheres, the difference between the major diameter (or maximum diameter) and the minor diameter (or minimum diameter) is less than 20%, less than 15%, less than 10%, less than 5%, or less than 1% depending on the embodiment used. The term "substantially spherical" can also refer to a microsphere having a major diameter/minor diameter ratio of from about 1.0 to about 2.0, from about 1.0 to about 1.5, or from about 1.0 to about 1.2.

As used herein, "swellable" microspheres refer to microspheres that are capable of being enlarged in size, yet retain substantially the same shape, upon certain conditions, such as contacting aqueous liquids or physiological fluids.

As used herein, "therapeutic agent" refers to any substance that provides therapeutic effects to a disease or symptom related thereto. In certain embodiments, a therapeutic agent refers to a substance that provides therapeutic effects to any of the processes of angiogenesis-dependent diseases or biological or physiological responses to the angiogenesis-dependent diseases. An example of a therapeutic agent is an anti-inflammation agent that prevents or reduces the effect of inflammations associated with angiogenesis-dependent diseases.

As used herein, the term "therapy" refers to any protocol, method, and/or agent that can be used in the management, treatment, and/or amelioration of a given disease, or a symptom related thereto. In certain embodiments, the terms "therapies" and "therapy" refer to a biological therapy, supportive therapy, and/or other therapies known to one of skill in the art, such as medical personnel, useful in the management or treatment of a given disease, or symptom related thereto.

As used herein, "treat," "treatment," and "treating" refer to the reduction or amelioration of the progression, severity, and/or duration of a given disease resulting from the administration of one or more therapies (including, but not limited to, the administration of microspheres disclosed herein). In certain embodiments, the terms refer to the reduction of pain associated with one or more diseases or conditions.

Microspheres

As further detailed herein, in some embodiments, the present disclosure relates to microspheres suitable for drug delivery and/or therapeutic embolization. In an embodiment, the microspheres comprise a polymeric material. The polymeric material may comprise a copolymer comprising an acrylic monomer (and/or another monomer) and a cyclodextrin or a derivative thereof. The microspheres may also comprise a therapeutic agent. In an embodiment, the therapeutic agent is an anti-neoplastic drug.

In some embodiments, the polymeric material is a biocompatible, polymeric material. Biocompatible, polymeric materials are non-toxic to tissues and cells and generally do not cause inflammation. The polymeric material also comprises at least one polymer, copolymer, or mixture thereof. Further, as can be appreciated, when reciting that the polymeric material comprises a particular monomer (e.g., an acrylic monomer), it will generally be understood that the polymeric material comprises a polymerized form of such a monomer.

Various types of polymeric materials can be used, including natural and/or synthetic polymeric materials. In some embodiments, the polymeric material comprises a copolymer comprising one or more acrylates, acrylamides, acrylics, vinyls, acetals, allyls, cellulosics, methacrylates, polyamides, polycarbonates, polyesters, polyimides, polyolefins, polyphosphates, polyurethanes, silicones, styrenes, and/or polysaccharides, or derivatives and/or mixtures thereof. In particular embodiments, the polymeric material comprises a copolymer comprising at least one of an acrylic monomer, acrylamide monomer, or vinyl monomer, or derivative thereof. Other polymerizable monomers can also be used.

In one embodiment, the polymeric material comprises a copolymer comprising an acrylamide monomer or a derivative thereof. For example, the polymeric material can comprise a copolymer comprising an acrylamide such as N-[tris(hydroxymethyl)methyl]acrylamide or a derivative thereof. Other acrylamides can also be used, including, but not limited to, methacrylamides, N,N'-methylenebis(acrylamide), diethyl aminoethyl acrylamide, and triethyl aminoethyl acrylamide and derivatives thereof. In further embodiments, the polymeric material comprises a copolymer comprising a mixture of two or more different monomers, such as acrylic monomers, acrylamide monomers, vinyl monomers, or derivatives and/or mixtures thereof. For example, the polymeric material can comprise a copolymer comprising a mixture of two or more of the herein-mentioned acrylamides or derivatives thereof, such as a mixture of N-[tris(hydroxymethyl)methyl]acrylamide and N,N'-methylenebis(acrylamide) or derivatives thereof. In some embodiments, the polymeric material can further comprise an acrylate, such as sodium acrylate. For example, in some embodiments, the polymeric material comprises one or more (or two or more) acrylamides (e.g., N-[tris(hydroxymethyl)methyl]acrylamide and N,N'-methylenebis(acrylamide)) and an acrylate (e.g., sodium acrylate). In some embodiments, the polymeric material lacks an acrylate monomer. Other monomer mixtures can also be used. For example, different monomers having different properties can be polymerized to achieve a copolymer having one or more desired properties.

The copolymer also comprises at least one cyclodextrin or a derivative thereof. For example, in certain embodiments, the copolymer comprises an α (alpha)-cyclodextrin or a derivative thereof. Other cyclodextrins or cyclodextrin derivatives can also be used, including, but not limited to, β (beta)-cyclodextrins and γ (gamma)-cyclodextrins and derivatives thereof. In further embodiments, the copolymer comprises a mixture of two or more cyclodextrins or derivatives thereof, such as two or more of the herein-mentioned cyclodextrins or derivatives thereof. As can be appreciated, α (alpha)-cyclodextrins can be used to describe six-membered sugar ring molecules, β (beta)-cyclodextrins can be used to describe seven-membered sugar ring molecules, and γ (gamma)-cyclodextrins can be used to describe eight-membered sugar ring molecules.

In some embodiments, the cyclodextrin is modified or functionalized such that it can be polymerized and incorporated into the polymeric material. For example, the cyclodextrin can be modified or functionalized to include a group or moiety that can be polymerized with another monomer (e.g., such as an acrylic monomer described herein) to form a copolymer. In particular embodiments, the cyclodextrin is modified or functionalized to include a group or moiety that can be polymerized with an acrylic monomer (and/or another monomer) and incorporated into the backbone or backbone chain of a copolymer. In some embodiments, the cyclodextrin is modified to include an olefin.

In one embodiment, the modified cyclodextrin is selected from the group consisting of N-propenoyl-1-(6-deoxy-β-D-cyclodextrin-4-aminomethyl-1,2,3 triazole, N-propenoyl-1-(6-O-hexyl-β-D-cyclodextrin)-4-aminomethyl-1,2,3 triazole, and N-propenoyl-1-(6-hexylamino-6-deoxy-β-D-cyclodextrin-4-aminomethyl-1,2,3 triazole or mixtures thereof.

The cyclodextrin can be modified or functionalized in various ways, some of which are illustrated below. However, it will be appreciated that the reaction mechanisms detailed below are illustrative and not meant to be exhaustive or limiting in any way. In some embodiments, a tosyl chloride, N-tosylimidazole, mesyl chloride, or other like compound (e.g., sulfonyls etc.) can be reacted with a cyclodextrin. In some embodiments, the tosyl chloride, N-tosylimidazole, mesyl chloride, or other like compound is added to the cyclodextrin at a molar ratio of between 1:1 and 3:1.

In some embodiments, this step of modifying a cyclodextrin with a tosyl chloride, N-tosylimidazole, mesyl chloride, or other like compound is carried out in an aqueous or organic solvent. For example, in some embodiments, this step is carried out in a solvent that comprises or consists of water, pyridine, or a combination thereof. In some embodiments, this step is carried out at a temperature of between 10° C. and 60° C., such as between 15° C. and 55° C. In some embodiments, the reaction is carried out for between one hour and 48 hours (e.g., between 2 hours and 24 hours). In some embodiments, one or more of N,N'-dicyclohexylcarbodiimide (DCC), 4-dimethylaminopyridine (DMAP), or NaOH serves as a reagent during this step.

The resulting tosylate groups, mesylate groups, or other like groups (other sulfonate groups, etc.) can then be displaced by an azide (or other like compound) and subjected to a click reaction, such as a click reaction with an alkyne containing an acrylic group (or other polymerizable group) to form a modified or functionalized cyclodextrin as shown below:

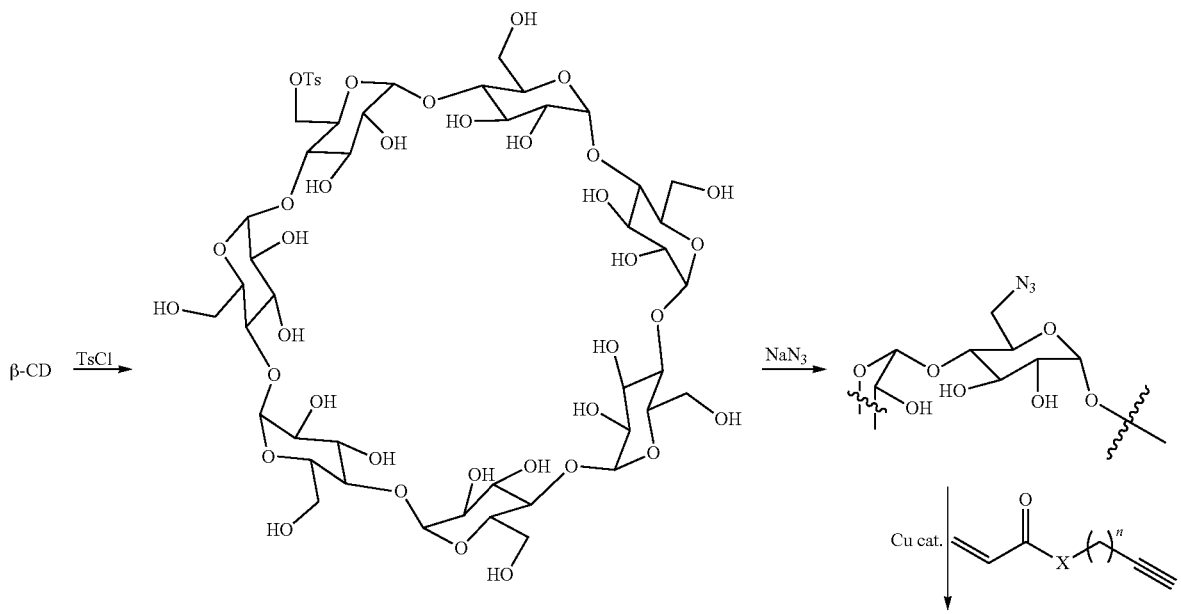

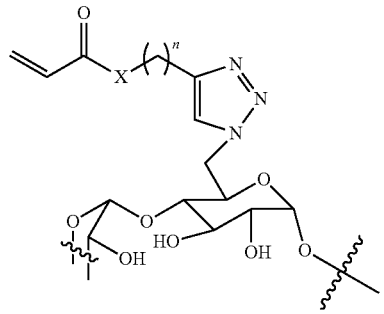

15 wherein X can be NR$^1$ or O, wherein R$^1$ is selected from H or C1-C6 alkyl, and wherein n can be any integer from 2 to 20.

In some embodiments, the addition of azide is carried out in a solvent comprising or consisting of dimethylformamide (DMF). In other embodiments the addition of an azide is carried out in a solvent comprising or consisting of water. In some embodiments, the reaction is carried out at a temperature of between 15° C. and 80° C., such as between 10° C. and 30° C. or between 70° C. and 90° C. The click reaction of an alkyne with an azide can be carried out in any suitable solvent (e.g., dimethyl sulfoxide (DMSO)) and can include one of more catalysts, such as a Cu$^{2+}$ catalyst (e.g., CuSO$_4$).

The alkyne, may be any suitable alkyne, such as N-(prop-2-yn-1-yl)acrylamide.

In another embodiment, the cyclodextrin can be modified or functionalized through use of a reduction reaction. For example, tosyl chloride, mesyl chloride, or other like compound (e.g., sulfonyls etc.) can be reacted with a cyclodextrin. The resulting tosylate groups, mesylate groups, or other like groups (other sulfonate groups, etc.) can then be displaced by an azide (or other like compound) and reduced to an amine (or other like group), which can be further reacted with a compound containing an acrylic group (or other polymerizable group), such as acryloyl chloride, to form a modified or functionalized cyclodextrin as shown below:

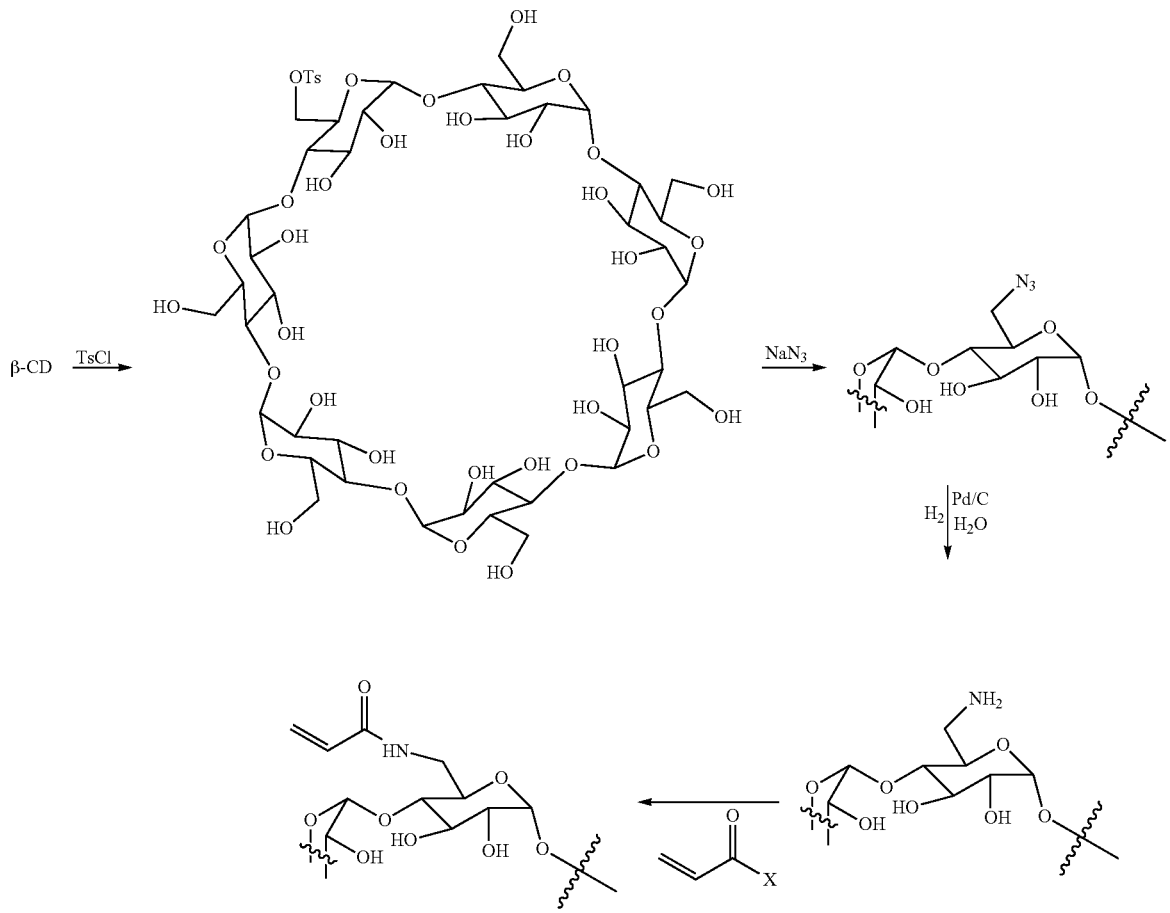

wherein X can be OH or a halogen such as Cl.

In some embodiments, the reduction step is carried out in the presence of palladium on carbon (Pd/C). In other embodiments, the reduction step is carried out in the presence of a phosphine (e.g., triphenylphosphine). In other words, in some embodiments, an azide may be reduced to an amine via a Staudinger reduction.

In another embodiment, the cyclodextrin may be modified or functionalized via an amination reaction. For example, in some embodiments, a tosylated cyclodextrin is modified by the addition of a primary amine. In some embodiments, this step is carried out in a microwave oven. In some embodiments, this reaction is carried out in a solvent such as DMF.

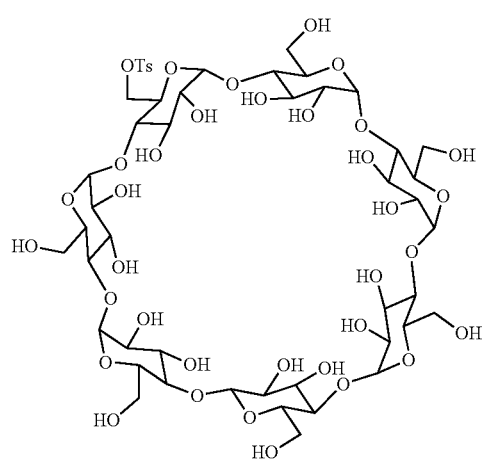

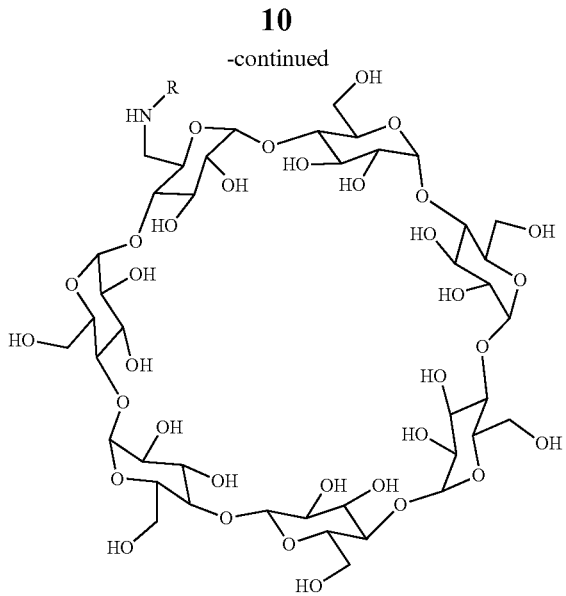

wherein R is a moiety containing at least one carbon atom.

In another embodiment, the cyclodextrin can be modified or functionalized through direct substitution of one or more hydroxyl groups (e.g., primary hydroxyl groups) on the cyclodextrin. For example, one or more hydroxyl groups (e.g., primary hydroxyl groups) can be directly substituted with an amine, diamine, or other like compound, which can be further reacted with a compound containing an acrylic group (or other polymerizable group), such as acryloyl chloride, to form a modified or functionalized cyclodextrin as shown below:

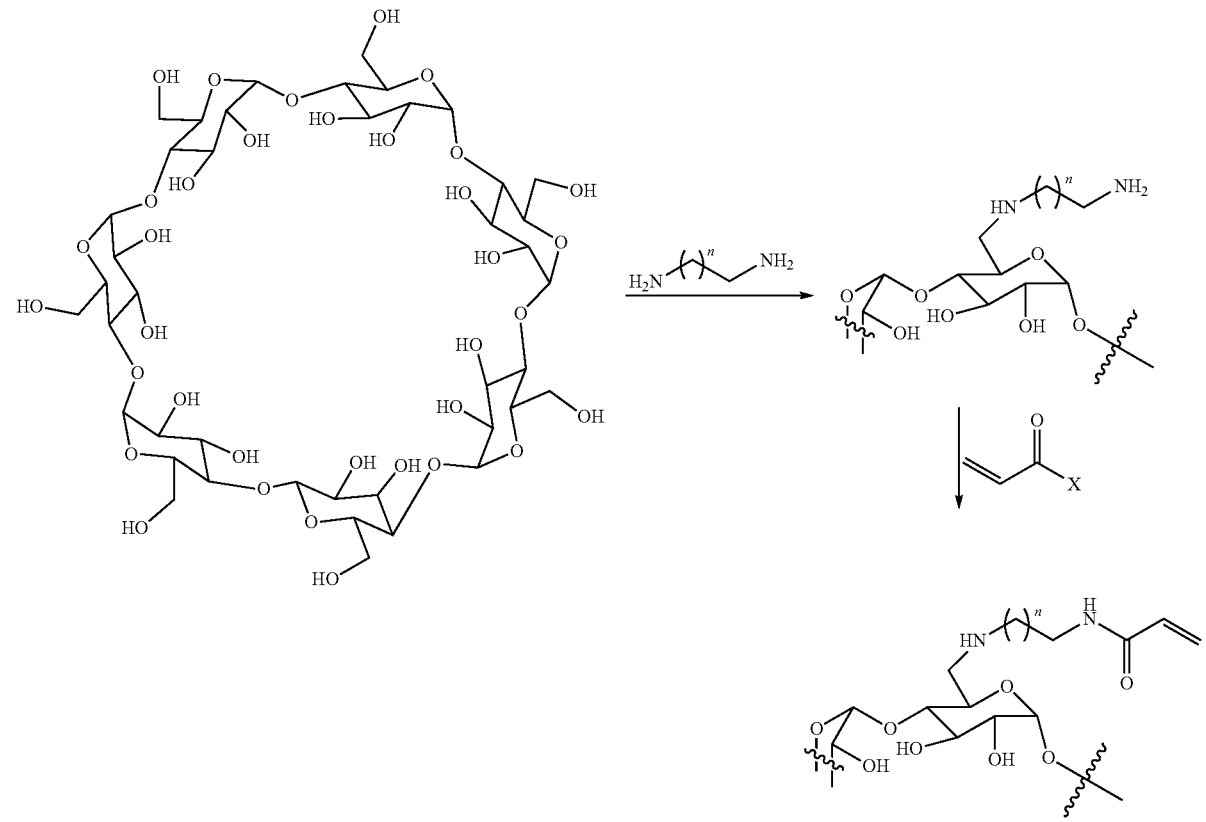

wherein X can be OH or a halogen such as Cl, and
wherein n can be any integer from 2 to 20.

In another embodiment, one or more hydroxyl groups (e.g., primary hydroxyl groups) can be directly substituted with an azane, ammonia, ammonium hydroxide, or other like compound, which can be further reacted with a compound containing an acrylic group (or other polymerizable group), such as acryloyl chloride, to form a modified or functionalized cyclodextrin as shown below:

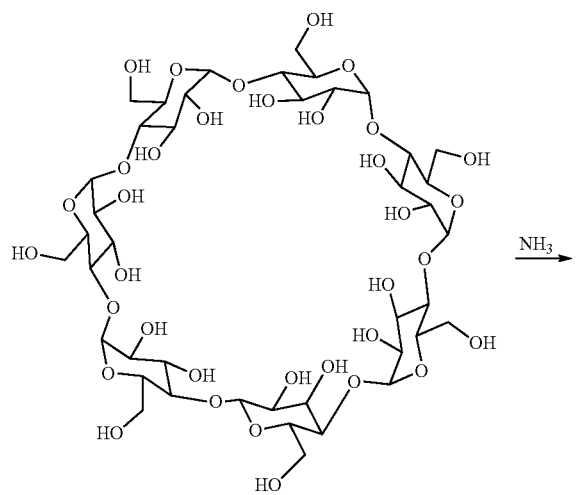

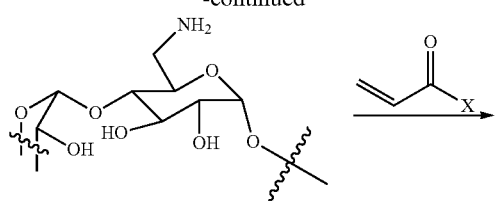

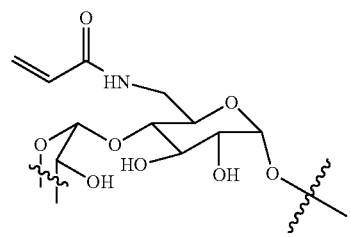

wherein X can be OH or a halogen such as Cl.

In some embodiments, one or more chain extenders (or spacers) can also be used. For example, one or more chain extenders can be included to increase the distance between the polymerized group and the cyclodextrin group of the functionalized cyclodextrin.

The cyclodextrin can be monofunctionalized, difunctionalized, or polyfunctionalized as desired. For example, the functionalization reactions, such as the above-mentioned functionalization reactions, can be performed once, twice, or more times to achieve a cyclodextrin having a desired number of functionalized groups. In some embodiments wherein the cyclodextrin is modified as a difunctional or polyfunctional cyclodextrin, the two or more polymerizable or functional sites can also cross-link the copolymer. An illustrative difunctionalized cyclodextrin having two polymerizable groups can be depicted as follows:

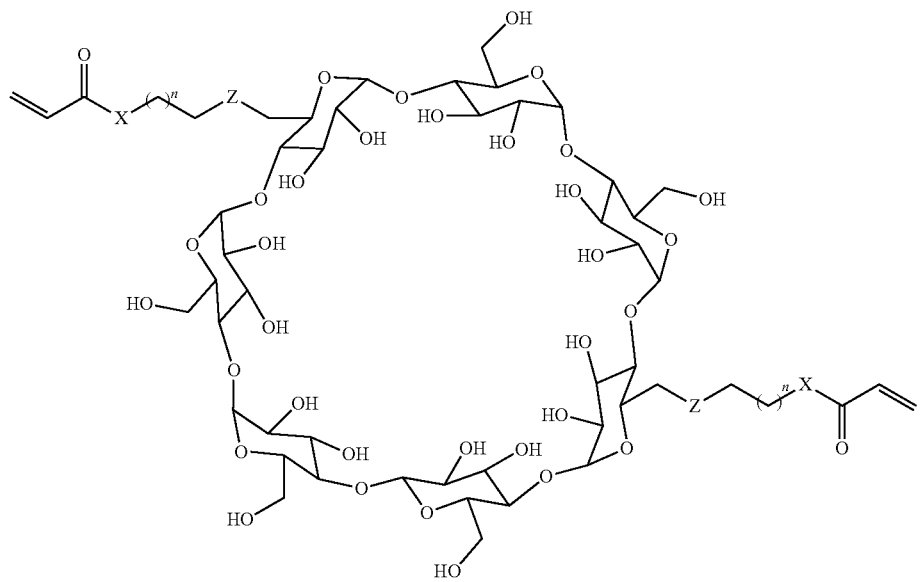

wherein X can be O or NR$^1$, wherein R$^1$ is selected from H or C1-C6 alkyl,
wherein Z can be O or NR$^2$, wherein R$^2$ is selected from H or C1-C6 alkyl, and
wherein n can be any integer from 2 to 20.

An illustrative polyfunctional cyclodextrin is depicted below. In such an example, each of the primary alcohol groups on the cyclodextrin has been substituted (fully substituted). One or more of the substituted groups can then be further modified as desired. For example, a polymerizable group can be added as follows:
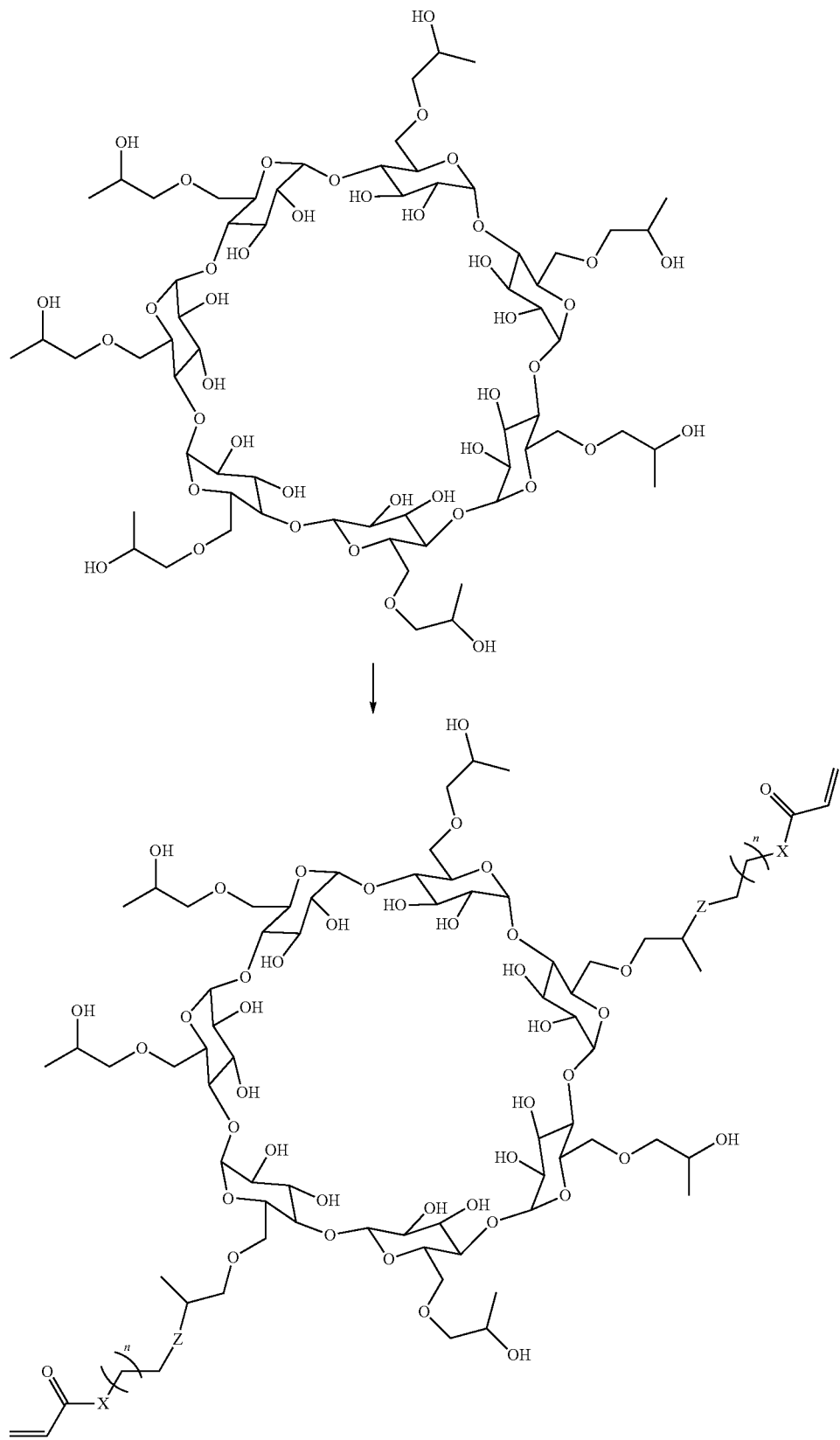

wherein X can be O or NR$^1$, wherein R$^1$ is selected from H of C1-C6 alkyl, wherein Z can be O or NR$^2$, wherein R$^2$ is selected from H of C1-C6 alkyl, and wherein n can be any integer from 2 to 20.

One or more protecting groups can also be used when modifying or functionalizing the cyclodextrin. For example, protecting groups or methods can be used to selectively functionalize a cyclodextrin. Illustrative protecting groups or methods include, but are not limited to, selective debenzylation methods. An illustrative selective debenzylation method that can be used to selectively functionalize a cyclodextrin can be depicted as follows:

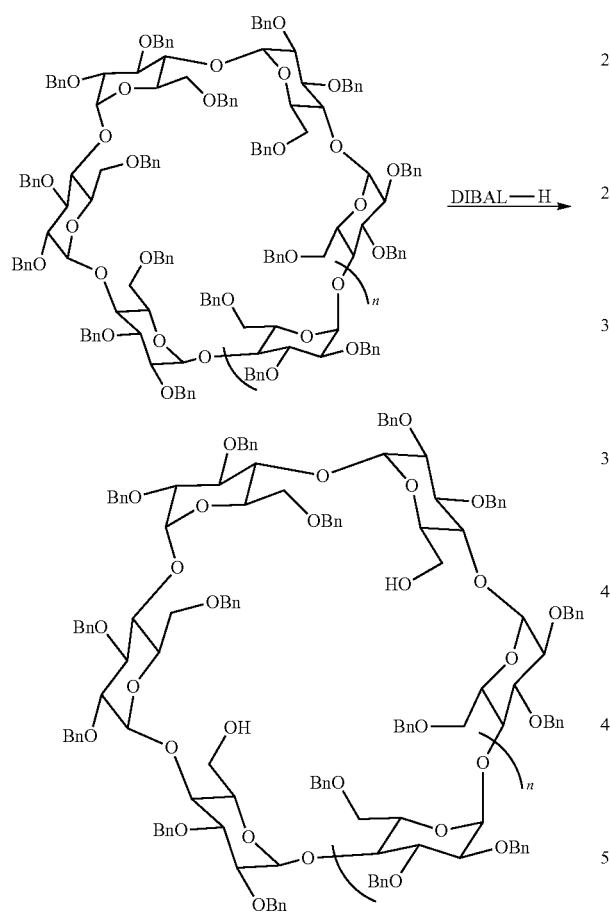

n = 1 or 2

Further modification of the selected hydroxyl groups can then be performed to selectively add polymerizable groups at the selected sites.

Other types of protecting groups and/or selective functionalization methods can also be used. For example, in one embodiment a capping moiety (or other protecting moiety) can be used. Various types of capping moieties and/or protecting moieties can be used. In some embodiments, a capping moiety or other protecting group can be used to bind the polymerizable group to a cyclodextrin as follows:

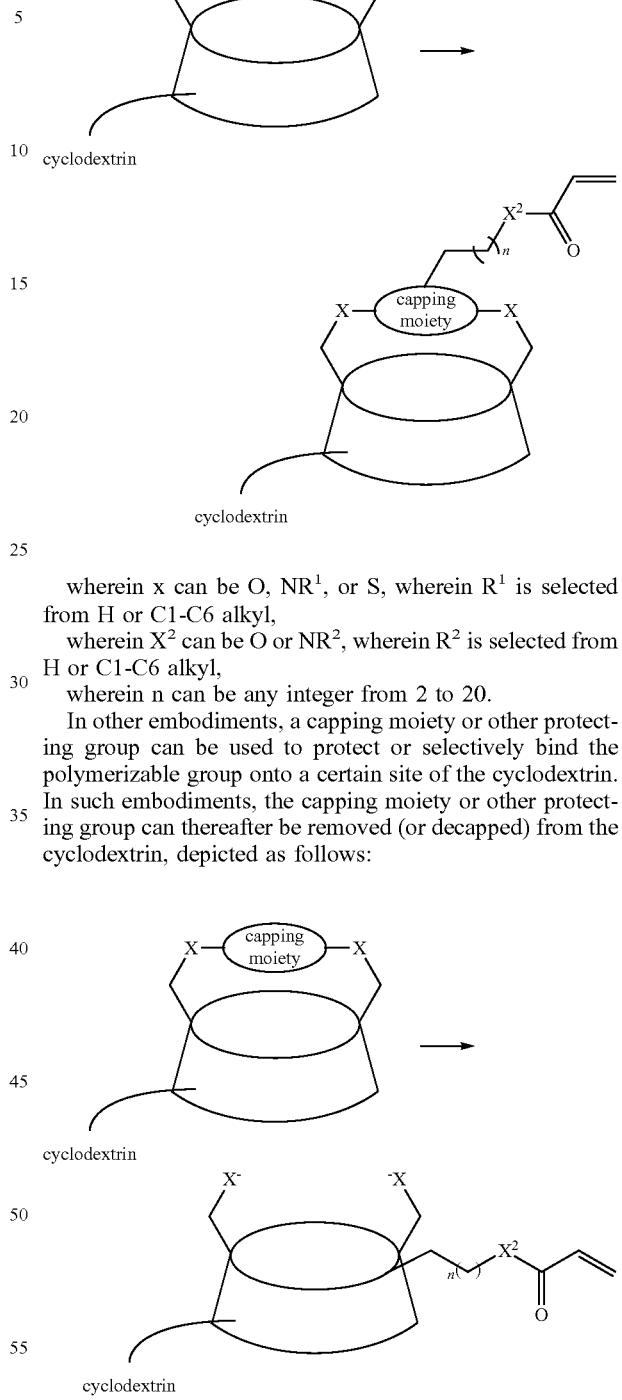

wherein x can be O, NR$^1$, or S, wherein R$^1$ is selected from H or C1-C6 alkyl, wherein X$^2$ can be O or NR$^2$, wherein R$^2$ is selected from H or C1-C6 alkyl, wherein n can be any integer from 2 to 20.

In other embodiments, a capping moiety or other protecting group can be used to protect or selectively bind the polymerizable group onto a certain site of the cyclodextrin. In such embodiments, the capping moiety or other protecting group can thereafter be removed (or decapped) from the cyclodextrin, depicted as follows:

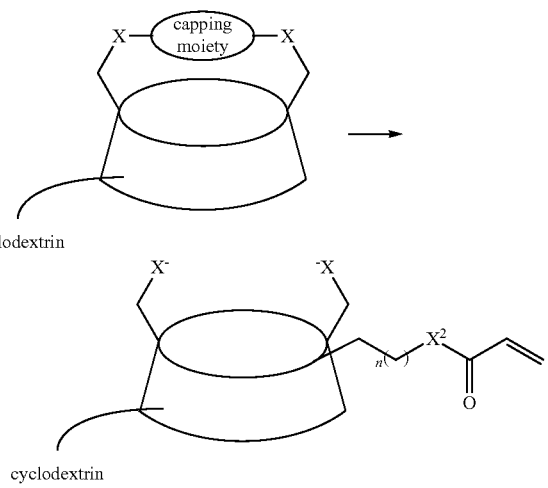

wherein X$^2$ can be O or NR$^2$, wherein R$^2$ is selected from H or C1-C6 alkyl, wherein x can be O, NR$^1$, or S, wherein R$^1$ is selected from H or C1-C6 alkyl, wherein n can be any integer from 2 to 20.

As can be appreciated, a modified and/or functionalized cyclodextrin can then be polymerized with one or more other monomer units, such as any of the herein-identified monomers. For example, the modified and/or functionalized cyclodextrin can be polymerized such that it forms a segment of the polymer backbone. An illustrative polymerization of a functionalized cyclodextrin with other monomer units is illustrated as follows:

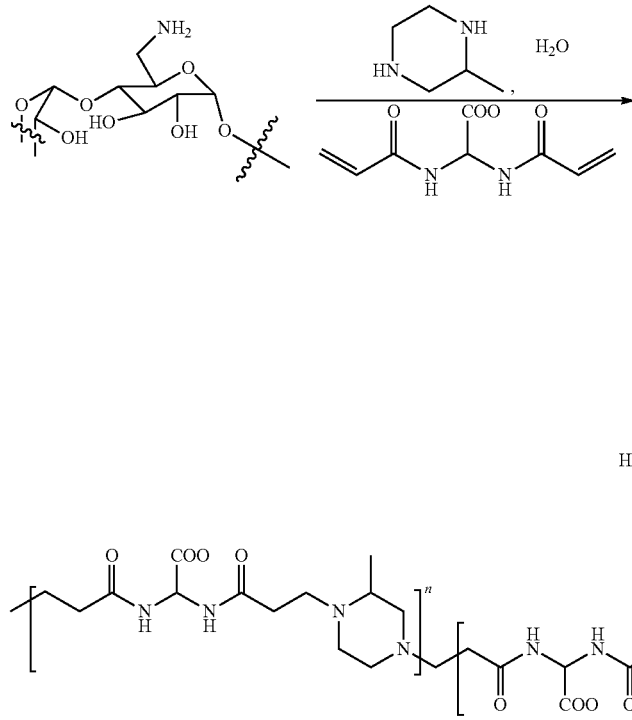
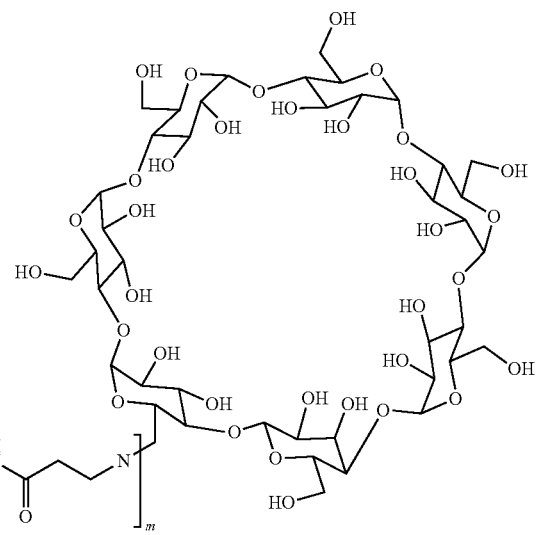

In certain embodiments, the polymeric material is cross-linked. For example, in some embodiments, the modified and/or functionalized cyclodextrin can function as a cross-linker. In other embodiments, the polymeric material can be cross-linked with a cross-linking agent. In some embodiments, the cross-linking agent comprises an aldehyde, such as, for example, glutaraldehyde or formaldehyde. In other embodiments, the cross-linking agent comprises an acrylamide, such as, for example, N,N'-methylene-bis-acrylamide, N',N'-diallylacrylamide, or glyoxal-bis-acrylamide. In further embodiments, the cross-linking agent comprises gelatin. Other types of cross-linking agents can also be used. In yet other embodiments, the polymeric material is not cross-linked.

The microspheres can also comprise a therapeutic agent. For example, the microspheres can be loaded with a therapeutic agent. In other words, the therapeutic agent can be adsorbed, absorbed, or otherwise associated with or bound to the microspheres. In a particular embodiment, the therapeutic agent associates with or otherwise interacts with a cyclodextrin group or moiety of the polymeric material. For example, the cyclodextrin group or moiety can comprise a ring or ring-like structure. The ring or ring-like structure can be substantially toroidal in shape. In some embodiments, the therapeutic agent can be at least partially loaded or disposed within the substantially toroidal shape. The therapeutic agent can also be described as being bound to the inside or inner surface of the ring or ring-like structure or toroidal shape. In other embodiments, the cyclodextrin group or moiety can be described as having a cavity disposed within the ring or ring-like structure. In such embodiments, the therapeutic agent can be at least partially loaded or disposed within the cavity of the ring structure.

In some embodiments, the therapeutic agent (e.g., drug) is loaded into dry microspheres at a ratio of from 0.05:1 to 10:1 by weight, from 0.1:1 to 10:1 by weight, from 1:2 to 5:1 by weight, or from 1:2 to 2:1 by weight. For instance, in some embodiments, 10 to 100 mg of therapeutic agent is loaded into 50 to 200 mg of dried microspheres. In some embodiments, a solution comprising therapeutic agent is combined with microspheres at a volumetric ratio of 1:1 to 100:1, or from 1:5 to 1:50. For example, in some embodiments, 1 mL to 2 mL of microspheres is added to 5 mL to 100 mL of a drug solution.

As further detailed herein, the therapeutic agent can be released from the microspheres when used in a therapeutic procedure. For example, in some embodiments, the cyclodextrin group or moiety degrades, is metabolized, or otherwise breaks down during a therapeutic procedure. For example, the cyclodextrin group or moiety can degrade, be metabolized, or break down in vivo when subjected to physiological conditions. In such embodiments, the therapeutic agent can be released from the microspheres as the cyclodextrin group or moiety degrades.

Various types of therapeutic agents can be used. For example, in some embodiments, the therapeutic agent comprises an anti-neoplastic drug, such as, for example, a chemotherapeutic drug. In particular embodiments, the therapeutic agent comprises a platinum-based drug or derivative thereof. For example, the therapeutic agent can comprise one or more of cisplatin, carboplatin, oxaliplatin, oxiplatin, satraplatin, picoplatin, nedaplatin, triplatin, lipoplatin, spiroplatin, iproplatin, and derivatives and mixtures thereof. Other platinum-based drugs or derivatives thereof can also be used. In one embodiment, the therapeutic agent comprises at least one of cisplatin, carboplatin, oxaliplatin, and oxiplatin. Other types of therapeutic agents can also be used. For example, in some embodiments, the microspheres comprise one or more taxols or derivatives thereof, such as one or more of docetaxel or paclitaxel. In another embodiment, the microspheres comprise one or more anthracyclines or derivatives thereof, such as one or more of doxorubicin, daunorubicin, epirubicin, idarubicin, valrubicin, and mitoxantrone. In another embodiment, the microspheres comprise one or more camptothecins or derivatives thereof, such as one or more of irinotecan, topotecan, exatecan, and lurtotecan. Mixtures of any of the herein-mentioned therapeutic agents can also be used. In further embodiments, the therapeutic agent comprises any therapeutic agent capable of being loaded or bound within the ring or ring-like structure of a cyclodextrin group or moiety.

In certain embodiments, the microspheres are spherical or substantially spherical in shape. The diameter of the microspheres may vary. For example, in some embodiments, the microspheres have an average diameter of from about 10 μm to about 2,000 μm, from about 30 μm to about 1,500 μm, from about 40 μm to about 1,200 μm, from about 40 μm to about 900 μm, from about 40 μm to about 600 μm, or from about 40 μm to about 400 μm.

The microspheres can also be substantially uniform in size. For example, the difference in diameter between individual microspheres can be from about 0 μm to about 250 μm, from about 0 μm to about 200 μm, from about 0 μm to about 150 μm, or from about 0 μm to about 100 μm. In further embodiments, individual microspheres have differences in diameter of 200 μm or less, 150 μm or less, 100 μm or less, about 50 μm or less, about 25 μm or less, about 10 μm or less, or about 5 μm or less. In particular embodiments, the microspheres are in a population wherein greater than 68% have a diameter of ±20% of the mean, ±10% of the mean, or ±5% of the mean diameter. In one embodiment, the microspheres are in a population wherein greater than 75% have a diameter of ±20% of the mean, ±10% of the mean, or ±5% of the mean diameter.

In some embodiments, the microspheres are substantially hydrophilic. For example, the microspheres can contain at least one hydrophilic polymer or copolymer. In some of such embodiments, the microspheres can also include one or more hydrophobic polymers or copolymers as long as the overall characteristic of the microspheres are substantially hydrophilic rather than hydrophobic. In some embodiments, the hydrophilic polymer or copolymer is a polymer or copolymer containing —OH and/or —NH$_2$ groups. In other embodiments, the hydrophilic polymer or copolymer contains ionic groups.

In certain embodiments, the microspheres are swellable and/or water swellable. For example, the microspheres can be swellable upon contact with a pharmaceutically acceptable liquid, such as water, buffer solutions, saline, body liquids, physiological fluids, and aqueous salt solutions. For example, in particular embodiments, the microspheres can swell such that they are enlarged to about 15 times their original size (i.e., diameter) or to about 3,375 times their original volume. In other embodiments, the microspheres can swell such that they are enlarged to about four times their original size (i.e., diameter) or 64 times in volume upon contact with saline (e.g., 0.9% sodium chloride solution). In certain embodiments, the microspheres can swell such that they are enlarged to at least about 110%, at least about 115%, at least about 120%, at least about 125%, at least about 130%, at least about 135%, at least about 140%, at least about 145%, or at least about 150% their original diameter upon contact with water.

In some embodiments, swellable microspheres refer to microspheres that have the ability to absorb water. For example, in certain embodiments, the water absorption rate of a swellable microsphere is at least about 750 g/g. The degree of swelling can be controlled by controlling factors such as, for example, the solvents in which the microspheres are suspended, and specific polymers or copolymers used to make the microspheres. In certain embodiments, the degree of crosslinking can be adjusted, and in other embodiments, cross-linking is not adjusted or is not present.

In some embodiments, the microspheres can also be flexible or elastic such that they can easily pass into and through injection devices and small catheters without being permanently altered. The microspheres can also be resistant to the muscle contraction stress generated during and after the implantation process. The microspheres can also be compressible.

The microspheres can also be substantially non-aggregating such that they do not clump together. Further, in some embodiments, the microspheres do not substantially adhere to the wads of storage containers and/or implantation devices, such as catheters, syringes, needles, and the like.

In some embodiments, the microspheres are substantially insoluble in pharmaceutically acceptable liquids, such as water, buffer solutions, saline, body liquids, and physiological fluids. In particular embodiments, the microspheres are substantially water insoluble. In further embodiments, a first portion of the microsphere is soluble and a second portion of the microsphere is insoluble in water and/or other pharmaceutically acceptable liquids. For example, the cyclodextrin groups or moieties can be soluble whereas the remaining portion of the copolymer can be insoluble in water and/or other pharmaceutically acceptable liquids. In some of such embodiments, the microspheres can retain their substantially spherical shape after degradation of the cyclodextrin groups or moieties.

In certain embodiments, the microspheres are non-resorbable and/or non-biodegradable. For example, in such embodiments, the microspheres are not capable of being eliminated by the immune or lymphatic system. In other embodiments, the microspheres are resorbable and/or biodegradable. In yet other embodiments, a portion of the microsphere is non-resorbable and/or non-biodegradable while a second portion of the microsphere is resorbable and/or biodegradable. For example, the cyclodextrin groups on the copolymer of the microspheres can be degradable and/or resorbable while the remainder of the copolymer remains non-resorbable. In some of such embodiments, the microspheres are non-resorbable and/or non-biodegradable after degradation of the cyclodextrin groups or moieties. In further embodiments, the microspheres, including the cyclodextrin groups and the remaining copolymer, are resorbable and/or biodegradable.

In some embodiments, the microspheres are configured for use an embolic agents. In some embodiments where a first portion of the microsphere is biodegradable and/or resorbable (e.g., a cyclodextrin-containing portion) but a second portion of the microsphere is non-biodegradable and/or non-resorbable, the microspheres may retain their function as embolic agents even after the first portion of the microsphere has been degraded. Stated differently, in some embodiments, the microspheres are configured to substantially prevent the flow of blood through a region of the vasculature, even after a therapeutic agent (or a portion thereof) has been released from the microspheres due to degradation of a cyclodextrin-containing portion of the microsphere. In some embodiments, the microspheres may completely prevent blood flow through a region of the vasculature. In other embodiments, the microspheres may decrease the flux of blood flow across a region of the vasculature by more than 80%, more than 90% and/or more than 95%. In some embodiments, the change in flux resulting from partial degradation of the microspheres is less than 5%. Stated differently, when administered to a patient, the microspheres may decrease the flux of blood flow across a region of the vasculature of the patient by 90% or more regardless of whether the biodegradable portion of the microsphere has been degraded.

In some embodiments, the microspheres further include or are used with marking agents. Exemplary marking agents include, but are not limited to, dyes, imaging agents, and contrast agents (e.g., ionic and non-ionic contrast agents).

In certain embodiments, the microspheres further include or are coated with agents which promote cell adhesion (e.g., cell adhesion promoters). For example, various types of cell adhesion promoters can be used. Exemplary cell adhesion promoters that can be used include, but are not limited to, collagen, gelatin, glucosaminoglycans, fibronectins, lectins, polycations (such as polylysine, chitosan, and the like), or any other natural or synthetic biological cell adhesion agent. In specific embodiments, living cells are attached to the microspheres, forming layers of cells therein or thereon that link with surrounding tissues and can enhance the long-term stability of the microspheres.

In some embodiments, the microspheres are sterile. The microspheres can also be thermally stable which allows for easy, convenient sterilization and room temperature, refrigerated, or frozen storage. The microspheres can also be stable in suspension, which allows the microspheres to be formulated and stored in suspension and injected with different liquids. For example, in some embodiments, the microspheres can be placed in suspension, and in particular, in the form of sterile and pyrogenic (pyrogen-free) injectable solutions, while avoiding the formation of aggregates or adhesion to the walls of storage containers and implantation devices, such as catheters, syringes, needles, and the like.

Methods of Preparing the Microspheres

The present disclosure also relates to methods of preparing or manufacturing the microspheres. For example, in some embodiments, the method comprises polymerizing a monomer composition comprising a monomer (e.g., such as an acrylic monomer, an acrylamide monomer, and/or another monomer described herein) and a cyclodextrin or a derivative thereof (e.g., such as a cyclodextrin described herein). The monomer composition may be polymerized according to various polymerization methods, including, but not limited to, suspension polymerization methods and drop-by-drop polymerization methods. In certain embodiments, the microspheres can be prepared in accordance with the polymerization methods described in French Patent No. 2,378,808 or U.S. Pat. Nos. 5,648,100, and 5,635,215, each of which is incorporated herein by reference.

In some embodiments, the microspheres are prepared by adding the monomer composition to an oil or other organic phase. Exemplary oils include, but are not limited to, mineral oils, paraffin oils, silicon oils, etc. In particular embodiments, the oil is heated before adding the monomer composition to the oil. For example, the oil can be heated to a temperature of from about 20° C. to about 100° C., or from about 30° C. to about 80° C. In certain embodiments, after adding the monomer composition to the oil, the resulting suspension is stirred during which the monomer composition is allowed to polymerize and microspheres are formed. In particular embodiments, the speed at which the suspension is stirred will change the distribution of the diameters of the microspheres that are formed. As can be appreciated, the monomer composition or the organic phase (e.g., oil) can also include various additives and/or additional agents, including, but not limited to, cross-linking agents, activating agents (e.g., N,N,N',N'-tetramethylethylenediamine), surfactants, salts, buffers, etc., and mixtures thereof.

In some embodiments, one or more cyclodextrin derivatives that are used to form the microspheres are configured for polymerization with one or more other monomers. For example, in some embodiments, a cyclodextrin derivative may include an olefin group that is suitable for polymerization with another olefin-containing monomer to form a backbone of a polymeric structure that forms the microsphere.

In other embodiments, microspheres are initially prepared from a polymer that is formed from monomers that do not contain cyclodextrin. After the microspheres (which lack cyclodextrin) have been formed, one or more cyclodextrin derivatives are then attached to the microspheres. In other words, in some embodiments, the initial formation of the microspheres does not involve a cyclodextrin-containing component. But once the microspheres are formed, one or more cyclodextrin derivatives are then attached to the microspheres.

For example, in some embodiments, microspheres are initially formed from monomers that do not include a cyclodextrin group, such as any of the above-identified non-cyclodextrin-containing polymers. The microspheres that are initially formed from monomers that lack a cyclodextrin group may include one or more functional groups that are configured to facilitate subsequent attachment of one or more cyclodextrin groups to the microspheres. For example, in some embodiments, the microspheres include a functional group selected from the group consisting of an alkyne, an amine, or a carboxylic acid/carboxylate.

In one embodiment, the microspheres include an alkyne functional group that reacts with an azide-Containing cyclodextrin derivative (e.g., via cock chemistry) to form a triazole adduct.

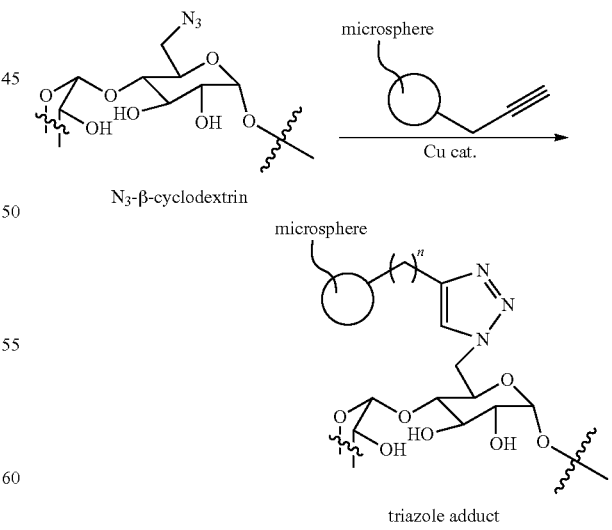

In another embodiment, the microspheres include a terminal amine functional group that reacts with a cyclodextrin derivative (e.g., a tosylated β-cyclodextrin), thereby attaching one of more cyclodextrin groups to each microsphere.

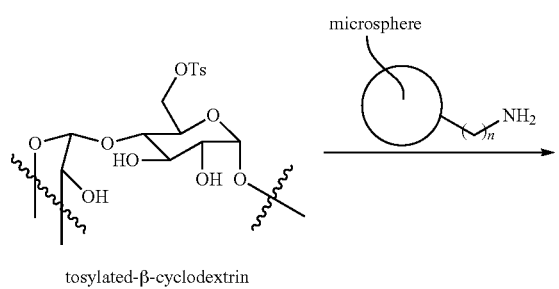
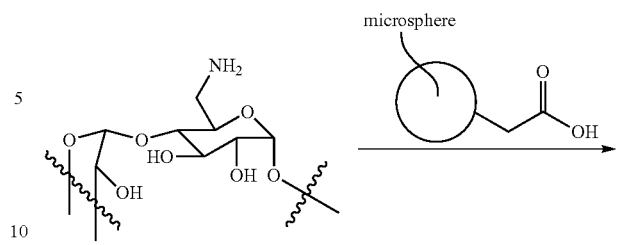

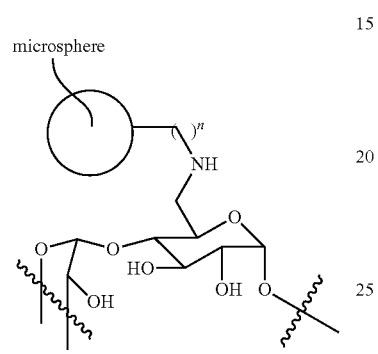

In some embodiments, the terminal amine functional group is attached to the microsphere via a spacer. The terminal amine then reacts with the derivatized cyclodextrin, thereby attaching one or more cyclodextrin groups to each microsphere.

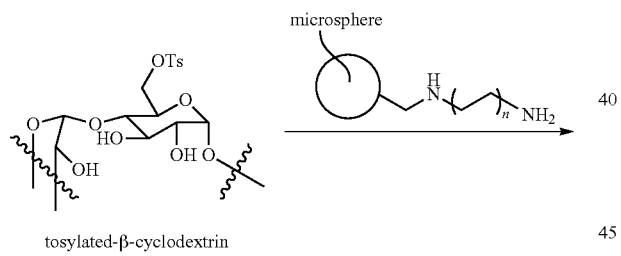

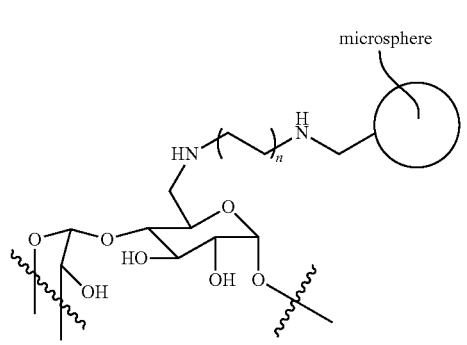

In some embodiments, the microspheres initially include a carboxylic acid or carboxylate functional group. The carboxylic acid/carboxylate group may be reacted with a terminal amine of a cyclodextrin derivative, thereby attaching one or more cyclodextrin groups to each microsphere.

In some embodiments, the microspheres are washed after polymerization and/or attachment to a cyclodextrin derivative. For example, the microspheres can be washed with water of an aqueous solution (e.g., a salt solution). In further embodiments, the microspheres are separated and/or sieved. For example, the microspheres can be sieved to obtain a population of microspheres having an average diameter within a desired range.

In some embodiments, the polymerized monomers (including the cyclodextrins) are dispersed throughout the body (or polymer body) of the microsphere. For example, the polymerized monomers (including the cyclodextrins) can be dispersed or distributed (e.g., uniformly or substantially uniformly) throughout the polymer matrix that forms the microsphere. In other embodiments, cyclodextrin groups are positioned only on the outer surfaces or outer regions of the microspheres, but are not found in interior regions of the microsphere.

In certain embodiments, the microspheres are loaded with a therapeutic agent. For example, the microspheres can be contacted with a therapeutic agent prior to use in a therapeutic procedure. In some embodiments, the microspheres are suspended in a liquid and a therapeutic agent is added to the suspension. In other embodiments, the microspheres are added to a solution comprising the therapeutic agent.

Pharmaceutical Compositions

The present disclosure also relates to pharmaceutical compositions comprising the microspheres disclosed herein. For example, in an embodiment, a pharmaceutical composition is disclosed that comprises microspheres and a pharmaceutically acceptable liquid or other biocompatible carrier. The compositions can be in the form of a suspension, a hydrogel, or an emulsion. For example, the composition can comprise a suspension of microspheres in a pharmaceutically acceptable liquid or other biocompatible carrier. In some embodiments, the compositions are sterile.

In certain embodiments, the pharmaceutically acceptable liquid can be, without limitation, saline, a buffer-solution, water, an isotonic solution, a biological fluid, or a mixture thereof. The liquid can also be a salt solution, such as a salt solution comprising cations selected from the group consisting of sodium, potassium, calcium, magnesium, iron, zinc, ammonium, and mixtures thereof, for example, in an amount of from about 0.01 M to about 5 M.

In some embodiments, a biocompatible carrier is used. The biocompatible carrier can comprise an aqueous-based solution, a hydro-organic solution, an organic solution, a non-aqueous solution, or a mixture thereof. In certain embodiments, the biocompatible carrier comprises a salt solution, such as a salt solution comprising cations, selected from the group consisting of sodium, potassium, calcium, magnesium, iron, zinc, ammonium, and mixtures thereof, for example, in an amount of from about 0.01 M to about 5 M.

Methods of Management and/or Treatment

The present disclosure also relates to methods of managing and/or treating a disease using the microspheres or pharmaceutical compositions disclosed herein. For example, in some embodiments, the microspheres and compositions are suitable for managing and/or treating tumors and/or other cancers, angiogenesis-dependent diseases, non-tumorigenic angiogenesis-dependent diseases, hepatocellular diseases, or pain, such as pain related to the presence of a tumor or other cancer. Such cancers include, without limitation, liver, ovarian, breast, kidney, lung, pancreatic, thyroid, prostate, uterine, skin cancer, head and neck tumors, breast tumors, Kaposi's sarcoma, and superficial forms of bladder cancer.

The microspheres and pharmaceutical compositions can be used in passive embolization therapies and in active embolization therapies. Embolization therapies (passive and active) can include using the microspheres to occlude or block a vessel such as a blood vessel. Active embolization therapies also include delivery of a therapeutic agent (e.g., a drug). For example, in active embolization therapies, the microspheres and compositions can have a dual function: mechanical blockage or occlusion (embolization) and localized delivery of a therapeutic agent to or near the occluded site.

The microspheres can also be used as delivery systems, for example, as delivery systems of a therapeutic agent or drug (e.g. drug-delivery systems), with or without embolization. For example, the method of management and/or treatment may be the result of localized (or systemic) delivery of a therapeutic agent (e.g., a drug) released from the microspheres, either alone or In combination with embolic effects of the microspheres (active embolization). In certain embodiments, microspheres loaded with a therapeutic agent (e.g., a drug) are administered to a site-specific location other than a blood vessel (e.g., directly into a tumor mass), and no vessel embolization occurs.

In certain embodiments, methods of management and/or treatment include administering to a mammal in need thereof a therapeutically effective amount of the microspheres or a pharmaceutical composition disclosed herein. The microspheres can be administered in a completely swollen or partially swollen state. In particular embodiments, the microspheres or compositions are suitable for administration by injection. For example, the microspheres or compositions can be injected using a needle attached to a syringe. In other embodiments, the microspheres or compositions are administered by a catheter. Administration can be into a blood vessel or directly to the site of action, for example into a tumor mass, or into a cell, organ, or tissue requiring such management and/or treatment.

In some embodiments, the microspheres or compositions are loaded with a therapeutic agent (e.g., a drug) prior to administration. In other embodiments, the microspheres or compositions are administered in combination with a drug solution, wherein the drug solution is administered prior to, simultaneously with, or after the administration of the microspheres. The microspheres can maintain their general shape and position once implanted at a desired site.

Kits

The disclosure further relates to pharmaceutical packs and kits comprising one or more containers filled with one or more of the ingredients of the aforementioned compositions. For example, the kits can comprise microspheres, and a solution comprising one or more therapeutic agents (e.g., drugs), wherein one, two, three, or more of the components can be in one, two, three, or more vials. Associated with such container(s) can be a notice in the form prescribed by a governmental agency regulating the manufacture, use, or sale of pharmaceuticals or biological products, reflecting approval by the agency of the manufacture, use, or sale of the product for patient (e.g., human or other mammal) administration. The reagents of any of the methods described herein can also be included as components of a kit.

In one kit format, the microspheres are present in a liquid, physiologically compatible solution in one vial. In another kit format, the microspheres can be provided in dry form in one vial and the therapeutic agent solution and optionally a contrast agent can be provided in a second and/or optionally a third vial. In certain embodiments, the microspheres, optionally comprising a contrast agent, are present in one vial, and the therapeutic agent is present in solution in another vial. In this form, the contents of the two vials can be mixed together prior to or concurrently with administration. In other embodiments, the microspheres comprising the therapeutic agent and optionally a contrast agent are provided in dry form in one vial. The powder can then be suspended in a suitable liquid prior to administration or a second vial is provided, which contains the injectable solution and the contents of both vials are combined prior to administration or concurrently with administration.

Finally, in another kit format the microspheres are present in one vial and a second vial contains a pharmaceutically acceptable solution optionally comprising a contrast agent. The microspheres in the first vial can be pre-loaded with a therapeutic agent, or the therapeutic agent solution can optionally be present in a third vial. The microspheres can then be mixed together with the therapeutic agent solution and/or pharmaceutically acceptable solution, for example, prior to or concurrently with administration.

EXAMPLES

Example 1—Synthesis of Mono-OTs-β-Cyclodextrin

NaOH (0.6 g, 15 mmol, 17 eq) was added to β-cyclodextrin (1.0 g, 0.88 mmol, 1 eq) that had been dissolved in water (20 mL). The resulting solution was stirred and then cooled to 0° C. Tosyl chloride (0.34 g; 2 eq) was then added to the solution. After about twelve hours, any remaining solid tosyl chloride was removed by filtration. Then an aqueous HCl solution (1 M) was added to the filtrate to a final pH of 6-7. The formed solid was recovered by filtration and recrystallized with water/acetonitrile (1:1) to afford mono-tosylated β-cyclodextrin.

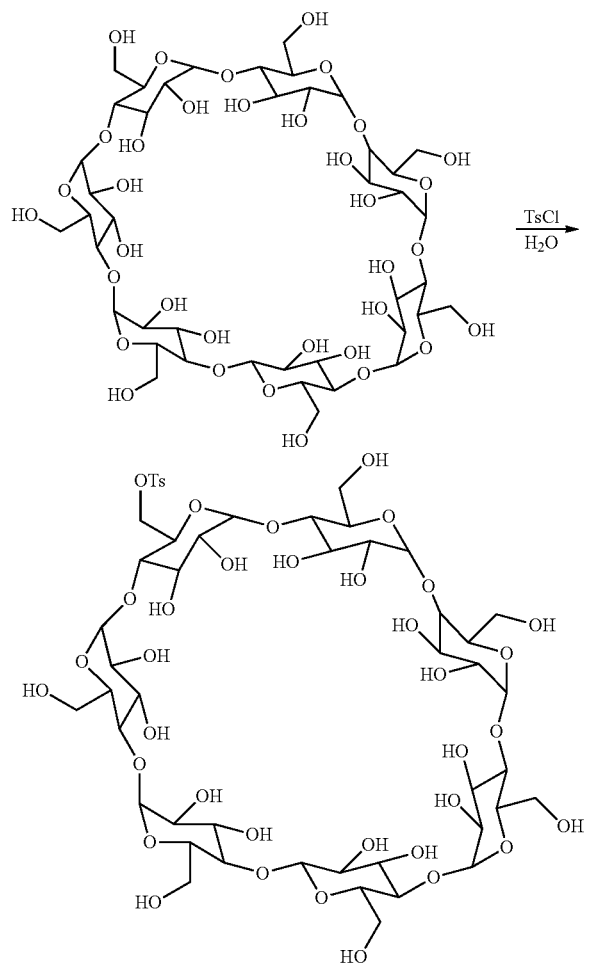

Example 2—Synthesis of Mono-OTs-β-Cyclodextrin

β-cyclodextrin (1.0 g, 0.88 mmol, 1 eq) was mixed with pyridine (16 mL) and stirred for 15 minutes. Meanwhile, in a separate flask, tosyl chloride (0.17 g, 0.88 mmol, 1 eq) and pyridine (1.2 mL) were mixed and stirred for 15 minutes. The β-cyclodextrin was then cooled to approximately 0° C., and the tosyl chloride solution was added to the cold β-cyclodextrin mixture. After approximately 24 hours of stirring, the pyridine was removed under reduced pressure. Acetone was then added to the mixture. The solid portion of the mixture was then collected by filtration and washed with cold water (2×5 mL) and acetone (2×10 mL) to afford mono-tosylated β-cyclodextrin.

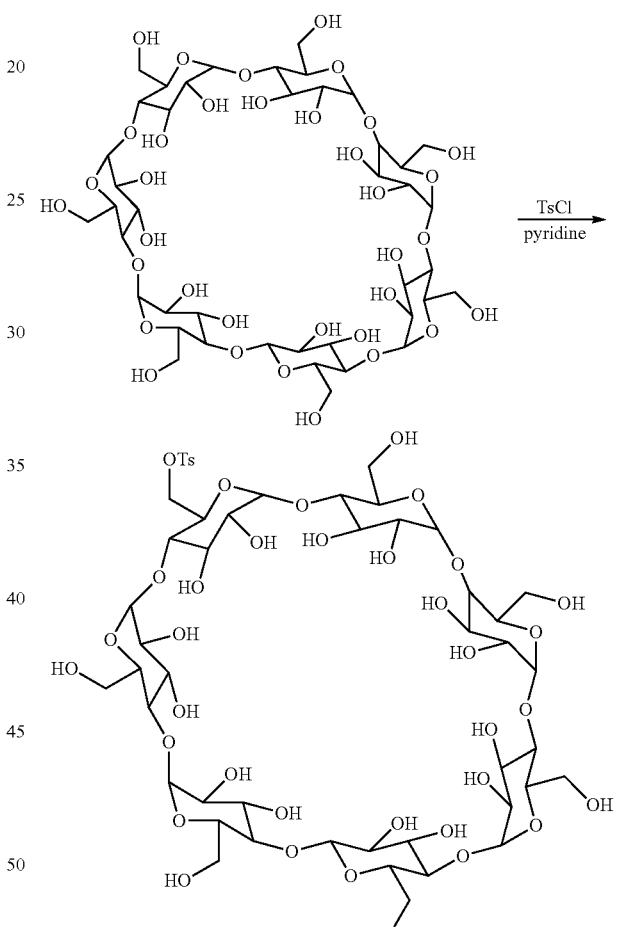

Example 3—Synthesis of Mono-OTs-β-Cyclodextrin

β-cyclodextrin (1.0 g, 0.88 mmol, 1 eq) was mixed with pyridine (16 mL) and stirred for 15 minutes. N,N'-dicyclohexylcarbodiimide (DCC) was then added (0.18 g, 0.88 mmol, 1 eq), and the mixture was stirred for an additional 15 minutes. Meanwhile, in a separate flask, tosyl chloride (0.17 g, 0.88 mmol, 1 eq) and pyridine (1.2 mL) were mixed and stirred for 15 minutes. The β-cyclodextrin mixture was then cooled to approximately 0° C., and the tosyl chloride solution was added to the cold β-cyclodextrin mixture. After approximately 24 hours of stirring, water (0.35 mL) was added, and then the liquid was evaporated. The resulting crude solid was precipitated with DMF/acetone (1:10) before being recrystallized with water to afford mono-tosylated β-cyclodextrin.

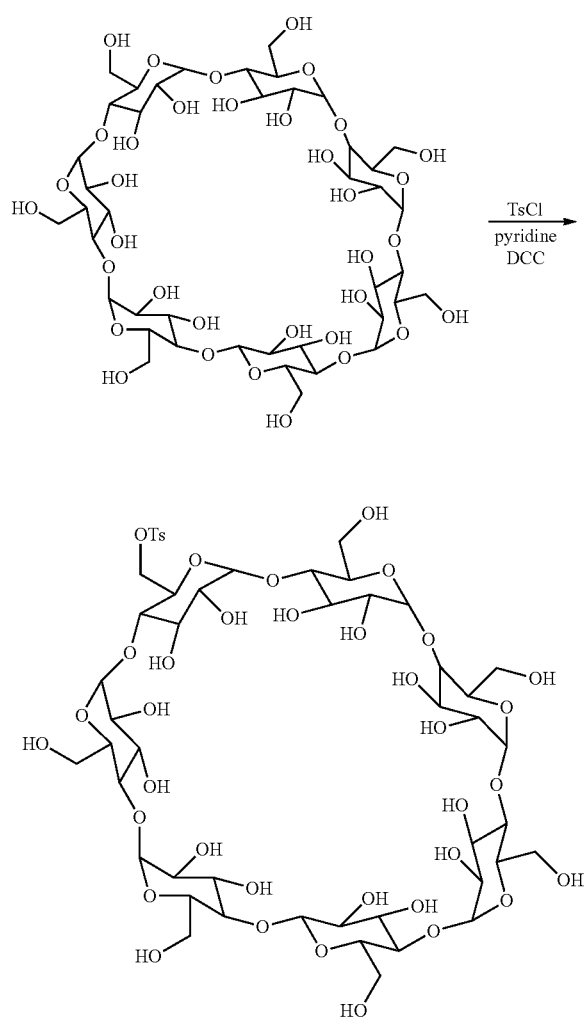

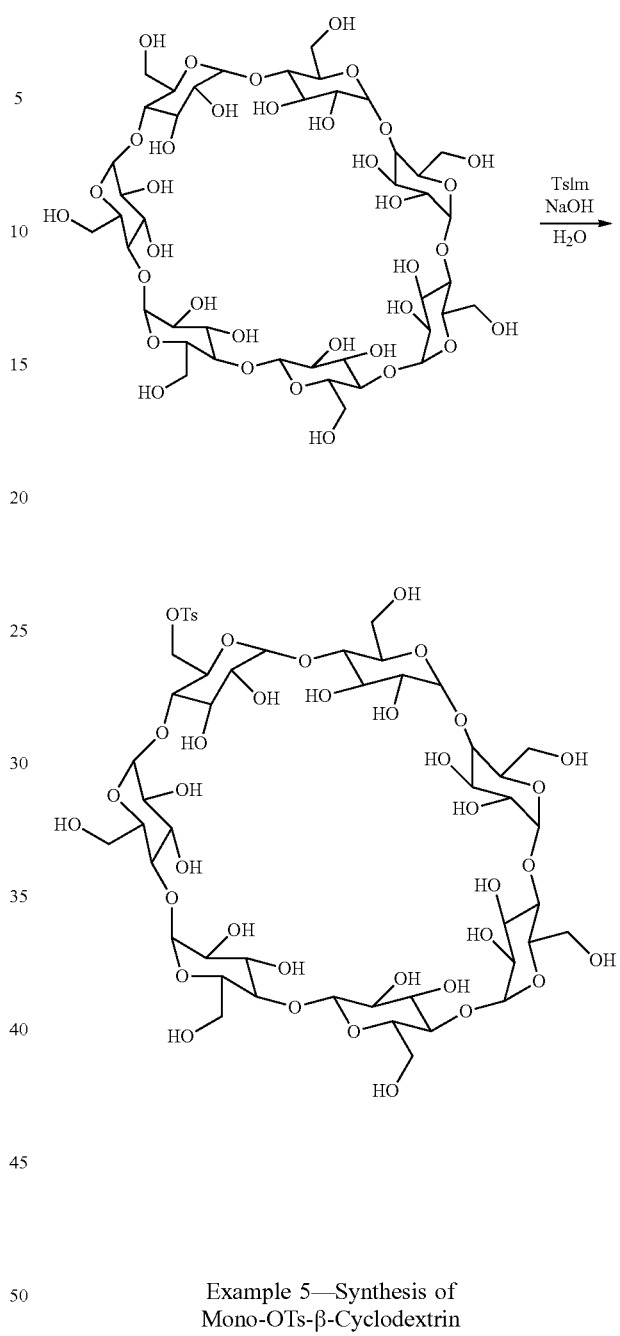

Example 4—Synthesis of Mono-OTs-β-Cyclodextrin

β-cyclodextrin (1.0 g, 0.88 mmol, 1 eq) was added into water (11 mL) and then stirred at 60° C. until fully dissolved. The solution was then cooled to 20° C., and tosylimidizole (0.35 mg) was added. The reaction was then stirred at room temperature for 2 hours, and NaOH (0.23 g) was added to the mixture. The mixture was then filtered, and NH$_4$Cl (0.64 g) was added to the filtrate. The mixture was then concentrated and again filtered. The resulting solid was washed with water (2×0.5 mL) and acetone (3 mL) to afford mono-tosylated β-cyclodextrin.

Example 5—Synthesis of Mono-OTs-β-Cyclodextrin

β-cyclodextrin (1.0 g, 0.88 mmol, 1 eq) was mixed with pyridine (12 mL) and stirred for 15 minutes. 4-dimethylaminopyridine (DMAP; 5 mol %) was then added, and the mixture was stirred for an additional 15 minutes. Meanwhile, in a separate flask, tosyl chloride (0.45 g, 2.3 mmol, 2.6 eq) and pyridine (1.2 mL) were mixed and stirred for 15 minutes. The β-cyclodextrin mixture was then cooled to approximately 0° C., and the tosyl chloride solution was added to the cold β-cyclodextrin mixture. After approximately 24 hours of stirring at 50° C., water (0.35 mL) was added, and then the liquid was evaporated. The resulting crude solid was precipitated with 1:10 DMF/acetone before being recrystallized with water to afford mono-tosylated β-cyclodextrin.

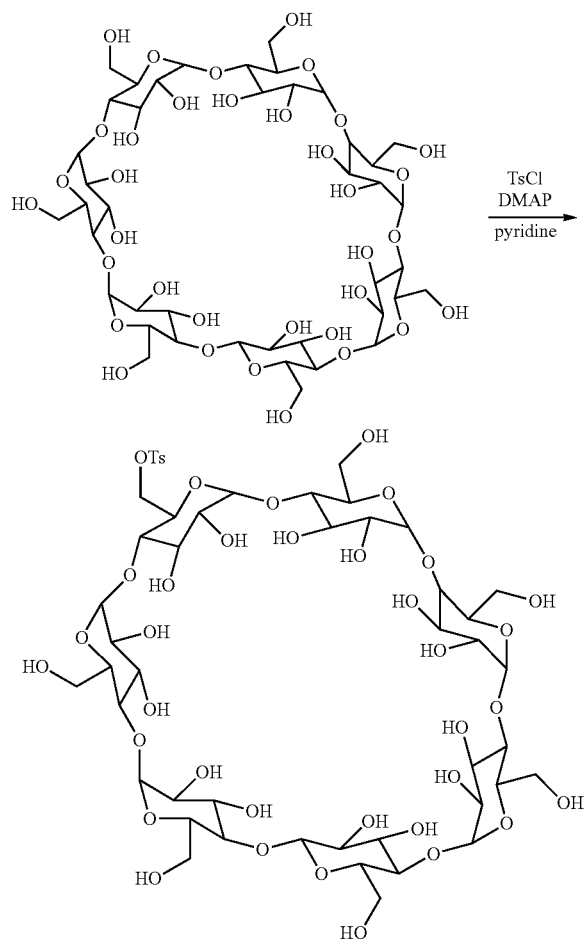

Example 6—Synthesis of Mono-N₃-β-Cyclodextrin

Mono-tosylated β-cyclodextrin (0.15 g) was dissolved in water (3 mL) and then stirred for 10 minutes before adding NaN$_3$ (0.06 g). The mixture was then heated to 80° C. for 12 hours. Then acetone (20 mL) was added to the mixture. After stirring, the mixture was filtered, and the collected solid was washed with water (2 mL) and acetone (10 mL) to afford mono-N$_3$-β-cyclodextrin.

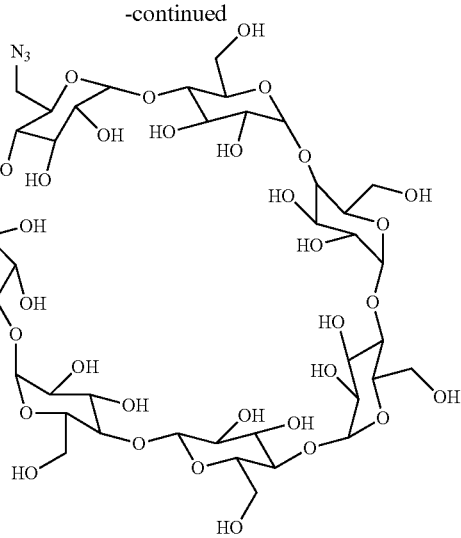

Example 7—Synthesis of Mono-N₃-β-Cyclodextrin

Mono-tosylated β-cyclodextrin (0.65 g) was dissolved in DMF (4 mL) and then stirred for 10 minutes before adding NaN$_3$ (0.16 g). The mixture was then heated to 75° C. for 24 hours. Then acetone (80 mL) was added to the mixture. After stirring, the mixture was filtered, and the collected solid was washed with acetone (3×10 mL) to afford mono-N$_3$-β-cyclodextrin.

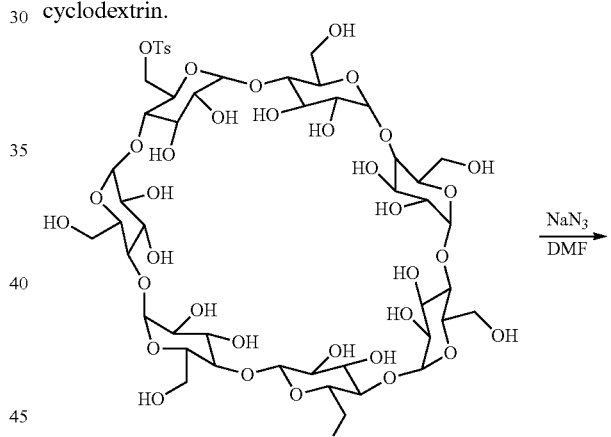

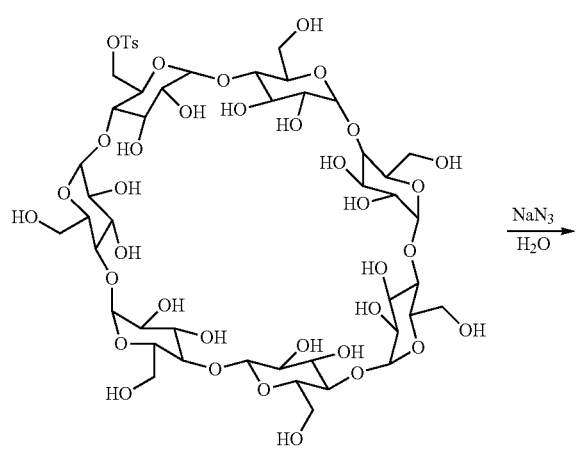

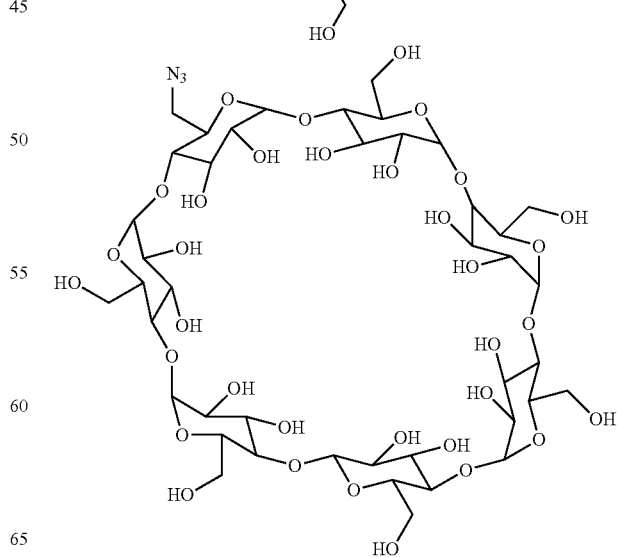

Example 8—Synthesis of Mono-NH$_2$-β-Cyclodextrin

Mono-tosylated β-cyclodextrin (0.1 g, 0.08 mmol) was placed in 1 mL of aqueous NH$_4$OH (28%) and heated at 60° C. for four hours. The reaction was then placed in a mixture of acetone:water (5.4:0.6) and stirred. A solid was recovered by filtration and washed with cold ethanol to afford mono-NH$_2$-β-cyclodextrin.

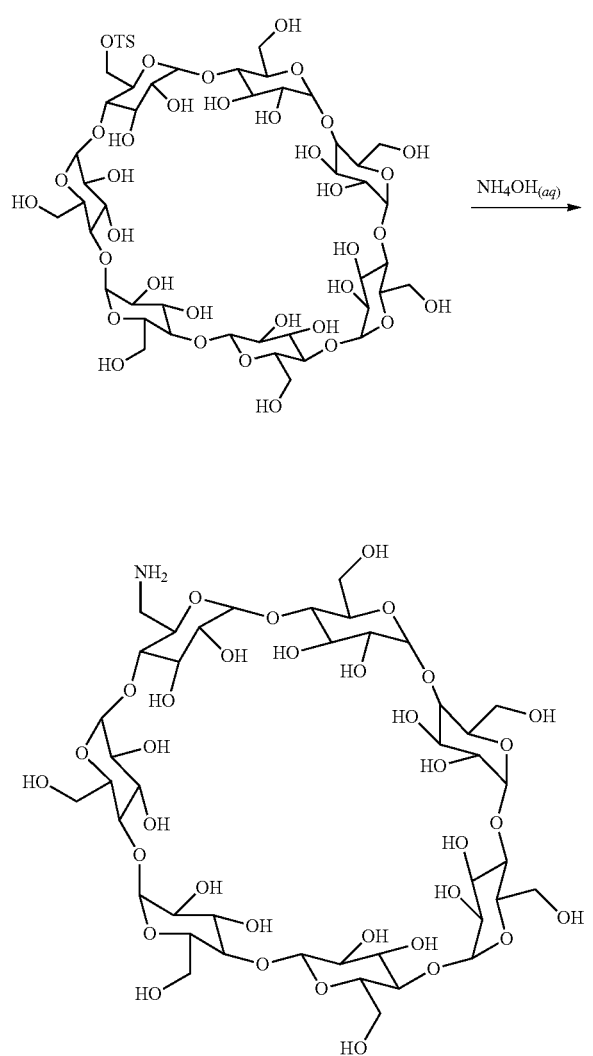

Example 9—Synthesis of Mono-NH$_2$-β-Cyclodextrin

Triphenyl phosphine (PPh$_3$; 0.175 g, 0.67 mmol) was added to a solution of mono-N$_3$-β-cyclodextrin (0.35 g, 0.3 mmol) in DMF (6 mL). The reaction was stirred for 4 hours at 20° C. and then poured into acetone. The resulting solid was recovered by filtration and washed with acetone to afford mono-NH$_2$-β-cyclodextrin.

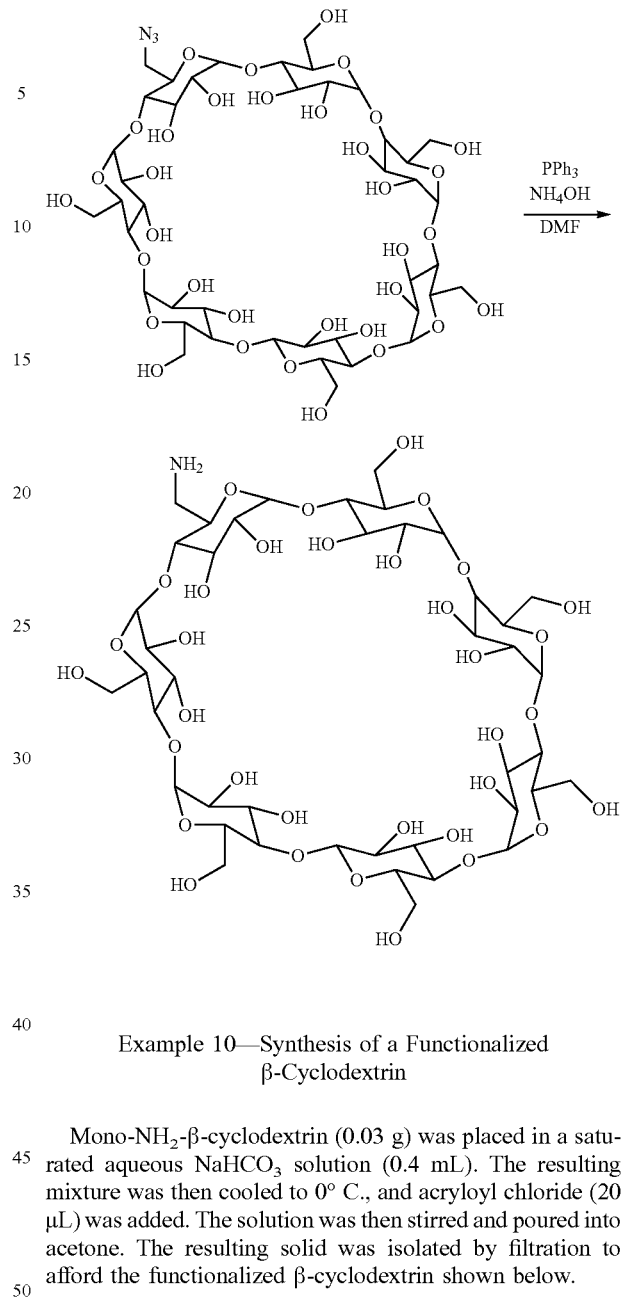

Example 10—Synthesis of a Functionalized β-Cyclodextrin

Mono-NH$_2$-β-cyclodextrin (0.03 g) was placed in a saturated aqueous NaHCO$_3$ solution (0.4 mL). The resulting mixture was then cooled to 0° C., and acryloyl chloride (20 μL) was added. The solution was then stirred and poured into acetone. The resulting solid was isolated by filtration to afford the functionalized β-cyclodextrin shown below.

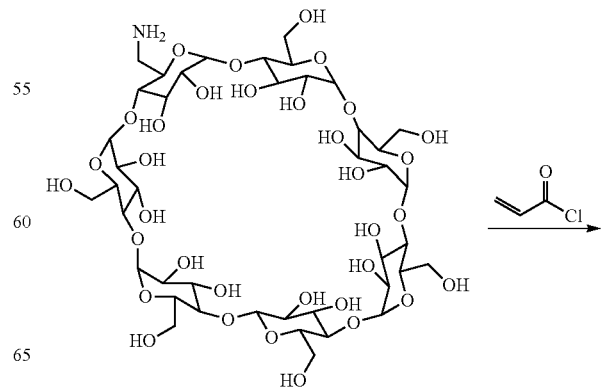

-continued

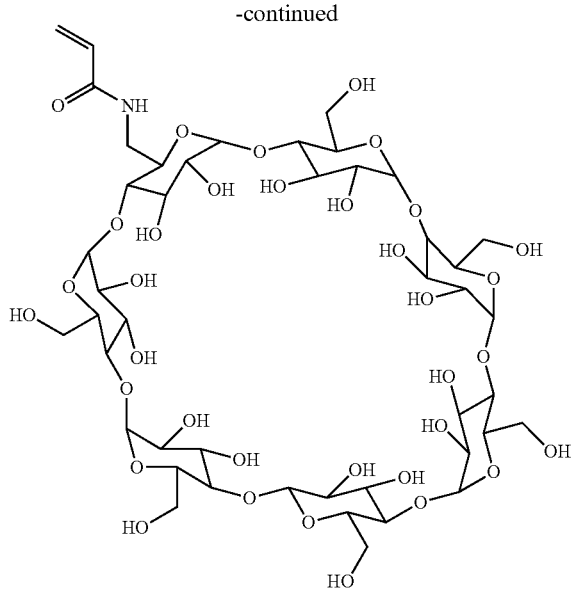

Example 11—Synthesis of N-propenoyl-1-(6-deoxy-β-D-cyclodextrin)-4-aminomethyl-1,2,3 triazole To a solution of N-(prop-2-yn-1-yl)acrylamide (0.28 g, 2.12 mmol) in DMSO (20 mL) was added mono-$N_3$-β-cyclodextrin (3.0 g, 2.5 mmol) and $CuSO_4$ pentahydrate (0.51 g, 2.12 mmol). Then sodium ascorbate (0.85 g, 4.3 mmol) that had been dissolved in water (2 mL) was added dropwise to the reaction mixture and stirred for 12 hours. The reaction was then precipitated in acetone (700 mL) and cooled to 4° C. The resulting solid was recovered by filtration to obtain a brown powder. The brown powder was then placed in aqueous $NH_4OH$ (8%) (20 mL) and stirred. The resulting composition was subjected to column chromatography to obtain N-propenoyl-1-(6-deoxy-β-D-cyclodextrin)-4-aminomethyl-1,2,3 triazole.

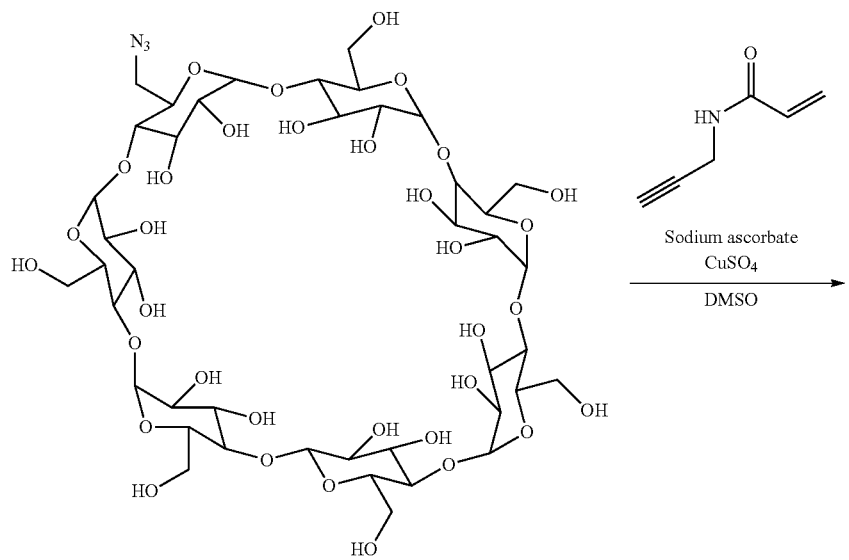

-continued

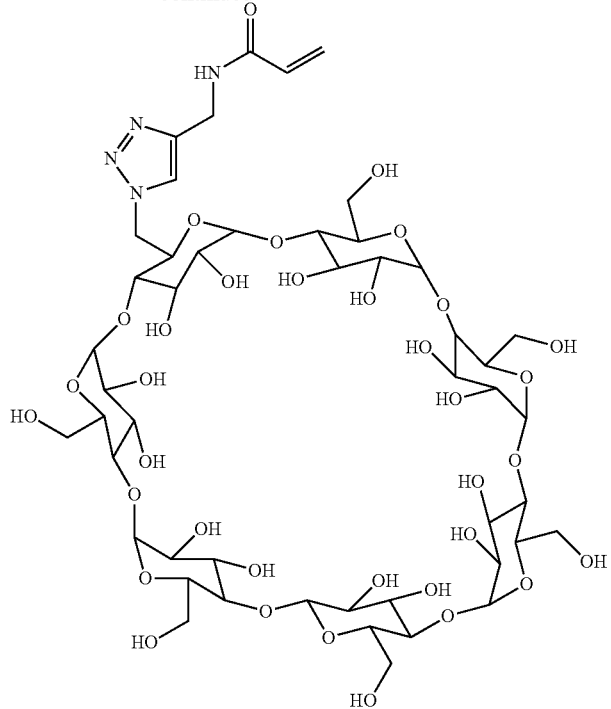

30

Example 12—Synthesis of N-(2-aminoethyl)acrylamide-β-cyclodextrin)

To a solution of mono-tosylated β-cyclodextrin (0.010 g, 0.008 mmol) in DMF (2 mL) was added N-(2-aminoethyl) acrylamide (0.130 g, 1.2 mmol) and the mixture was irradiated in a microwave oven for 30 minutes at 200 W and 85° C. Then acetone (50 mL) was added, and the precipitate was collected by filtration to afford N-(2-aminoethyl)acrylamide-β-cyclodextrin).

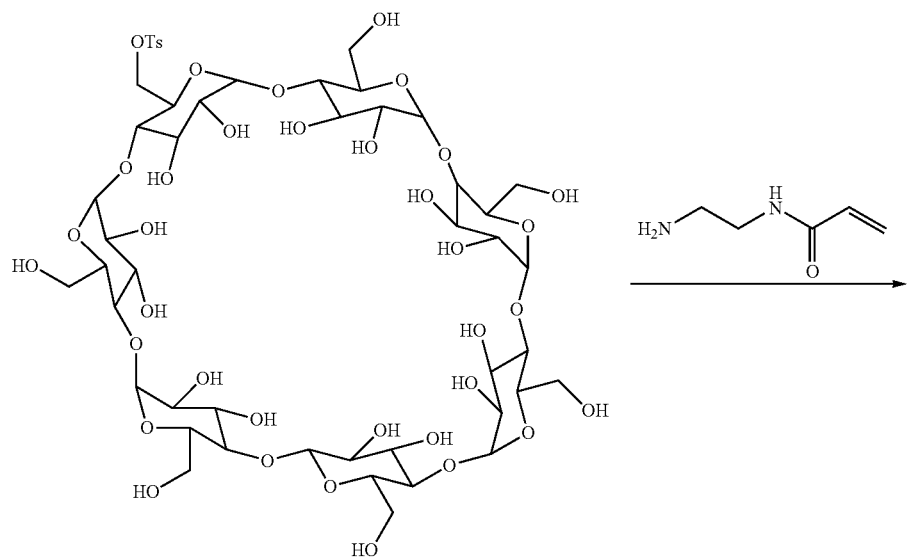

-continued

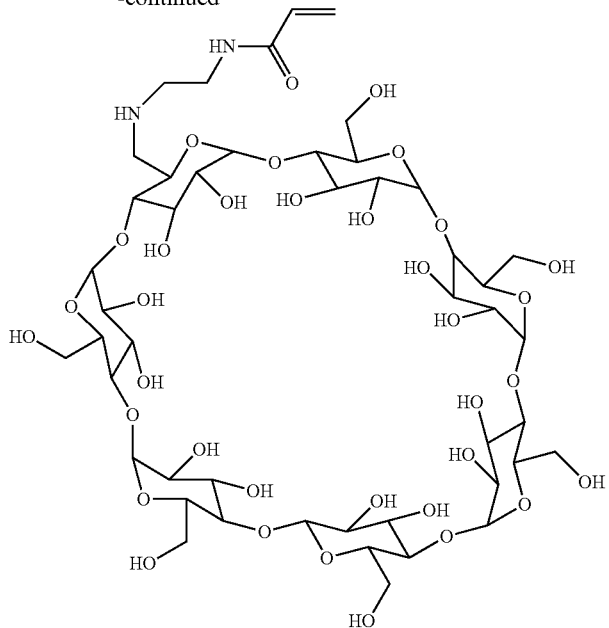

Example 13—Microsphere Synthesis

Microspheres can be prepared using a suspension polymerization process as follows: An aqueous monomer solution (solubilized in water) is prepared, which includes (1) 90 g of N-[tris(hydroxymethyl)methyl]acrylamide as a first monomer, (2) 30 g of N-propenoyl-1-(6-deoxy-β-D-cyclodextrin)-4-aminomethyl-1,2,3 triazole as a cyclodextrin derivative, and (3) 10 g of N,N'-methylenebis(acrylamide) as a crosslinking agent. Water is then added to adjust the total volume to 500 mL, and the aqueous monomer solution is warmed to 60° C. To the aqueous monomer solution is added 5 mmol of ammonium persulfate in 15 mL of water. The mixture is then briefly stirred to achieve homogeneity.

In a similar manner, the aqueous solutions of Table 1 are prepared:

A ten-liter beaker equipped with an overhead stirrer is then charged with four liters (L) of mineral oil and a surfactant (e.g., Arlacel 85) (1% in weight). The aqueous monomer solution is then added to the warmed oil solution (e.g., warmed to 60° C.) with vigorous stirring. 10 mL of the activating agent tetraethylmethylenediamine (5 mmol) is then added, while stirring, to initiate polymerization of the monomer solution. When polymerization is complete, five liters of cold water are added, and the microspheres settle in the aqueous phase. The microspheres are then isolated by repeated washes with water to remove all the oil. For storage, sodium chloride is added to a final weight percent of 0.9%.

TABLE 1

| First monomer | Cyclodextrin-containing component | Crosslinking agent |
| --- | --- | --- |
| N-[tris(hydroxymethyl)methyl]acrylamide | N-propenoyl-1-(6-O-hexyl-β-D-cyclodextrin)-4-aminomethyl-1,2,3 triazole | N,N'-methylenebis(acrylamide) |
| N-[tris(hydroxymethyl)methyl]acrylamide | N-propenoyl-1-(6-hexylamino-6-deoxy-β-D-cyclodextrin)-4-aminomethyl-1,2,3 triazole | N,N'-methylenebis(acrylamide) |
| Methacrylamide | N-propenoyl-1-(6-deoxy-β-D-cyclodextrin)-4-aminomethyl-1,2,3 triazole | N,N'-methylenebis(acrylamide) |
| N-[tris(hydroxymethyl)methyl]acrylamide | N-propenoyl-1-(6-deoxy-β-D-cyclodextrin)-4-aminomethyl-1,2,3 triazole | N',N'-diallylacrylamide |

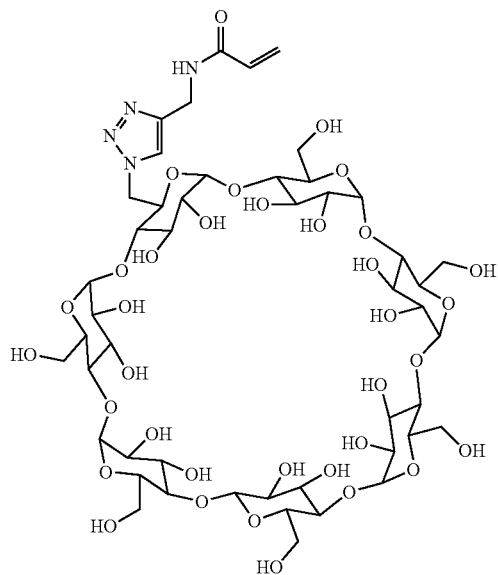

N-propenoyl-1-(6-deoxy-β-D-cyclodextrin)-4-aminomethyl-1,2,3 triazole

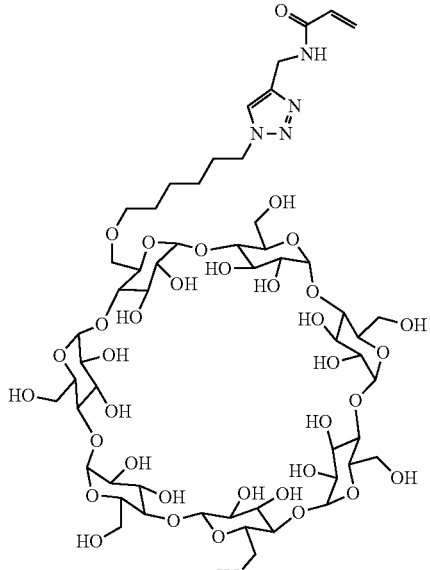

N-propenoyl-1-(6-O-hexyl-β-D-cyclodextrin)-4-aminomethyl-1,2,3 triazole

-continued

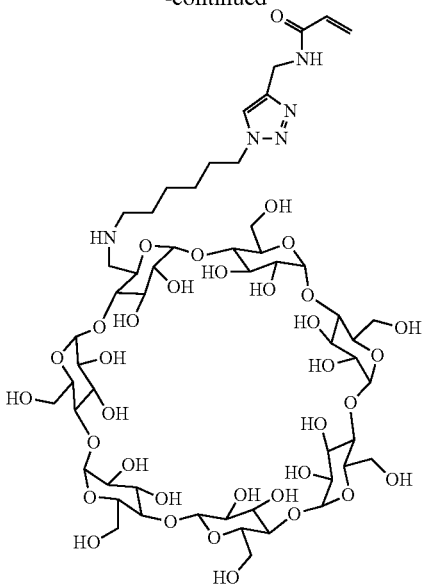

N-propenoyl-1-(6-hexylamino-6-deoxy-β-D-cyclodextrin)-4-aminomethyl-1,2,3 triazole Example 14—Microsphere Synthesis Microspheres are prepared using a suspension polymerization process as follows: An aqueous monomer solution (solubilized in water) is prepared, which includes (1) 60 g of N-[tris(hydroxymethyl)methyl]acrylamide as a first monomer, (2) 35 g of a sodium acrylate as a second monomer, (3) 30 g of N-propenoyl-1-(6-deoxy-β-D-cyclodextrin)-4-aminomethyl-1,2,3 triazole as a cyclodextrin-containing component, and (4) 10 g of N,N'-methylenebis(acrylamide) crosslinking agent. Water is then added to adjust the total volume to 500 mL, and the aqueous monomer solution is warmed to 60° C. To the aqueous monomer solution is added 5 mmol of ammonium persulfate in 15 mL of water. The mixture is then briefly stirred to achieve homogeneity.

In a similar manner, the aqueous monomer solutions of Table 2 are prepared.

TABLE 2

| First monomer | Second monomer | Cyclodextrin-containing component | Crosslinking agent |
|---|---|---|---|
| N-[tris(hydroxymethyl)methyl]acrylamide | Sodium acrylate | N-propenoyl-1-(6-deoxy-β-D-cyclodextrin)-4-aminomethyl-1,2,3 triazole | N,N'-methylenebis(acrylamide) |
| N-[tris(hydroxymethyl)methyl]acrylamide | Sodium acrylate | N-propenoyl-1-(6-O-hexyl-β-D-cyclodextrin)-4-aminomethyl-1,2,3 triazole | N,N'-methylenebis(acrylamide) |

TABLE 2-continued

| First monomer | Second monomer | Cyclodextrin-containing component | Crosslinking agent |
| --- | --- | --- | --- |
| N-[tris(hydroxymethyl)methyl]acrylamide | Sodium acrylate | N-propenoyl-1-(6-hexylamino-6-deoxy-β-D-cyclodextrin)-4-aminomethyl-1,2,3 triazole | N,N'-methylenebis(acrylamide) |
| Methacrylamide | Sodium acrylate | N-propenoyl-1-(6-deoxy-β-D-cyclodextrin)-4-aminomethyl-1,2,3 triazole | N,N'-methylenebis(acrylamide) |
| N-[tris(hydroxymethyl)methyl]acrylamide | Sodium acrylate | N-propenoyl-1-(6-deoxy-β-D-cyclodextrin)-4-aminomethyl-1,2,3 triazole | N',N'-diallylacrylamide |

A ten-liter beaker equipped with an overhead stirrer is then charged with four liters (L) of mineral oil and a surfactant (Arlacel 85) (1% in weight). The aqueous monomer solution is then added to the warmed oil solution (warmed to 60° C.) with vigorous stirring. About 10 mL of an activating agent (tetraethylmethylenediamine; 5 mmol) is then added, while stirring, to initiate polymerization of the monomer solution. Polymerization is evidenced by a mild exotherm (e.g., 3-5° C.). When polymerization is complete, five liters of cold water are added, and the microspheres settle in the aqueous phase. The microspheres are isolated by repeated washes with water to remove all the oil. For storage, sodium chloride is added to a final weight percent of 0.9%.

Example 15—Preparation of Drug-Loaded Microspheres

To 100 mg of dried microspheres is added 10 mL of a solution containing 10 mg of cisplatin. Due to contact with the drug solution, the microspheres swell, and the drug is chelated by the cyclodextrin of the microspheres. The microspheres can optionally be sterilized and then used for injection into a patient.

In a similar manner, microspheres are loaded with carboplatin, oxaliplatin, oxiplatin, satraplatin, picoplatin, nedaplatin, triplatin, lipoplatin, spiroplatin, and iproplatin, paclitaxel, and docetaxel.

Example 16—Preparation of Drug-Loaded Microspheres

To 1.5 mL of microspheres is added 7.5 mL of a cisplatin solution containing 10 mg of cisplatin. Due to contact with the drug solution, the microspheres swell, and the drug is chelated by the cyclodextrin of the microspheres. The microspheres can optionally be sterilized and then used for injection into a patient.

In a similar manner, microspheres are loaded with carboplatin, oxaliplatin, oxiplatin, satraplatin, picoplatin, nedaplatin, triplatin, lipoplatin, spiroplatin, and iproplatin, paclitaxel, and docetaxel.

References to approximations are made throughout this disclosure, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, FIGURE, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

What is claimed is:

1. Microspheres suitable for use in therapeutic embolization, comprising:
   a biocompatible, polymeric material comprising a copolymer comprising an acrylamide monomer, wherein the acrylamide monomer is selected from N-[tris(hydroxymethyl)methyl]acrylamide and N,N'-methylenebis(acrylamide), and a cyclodextrin; and
   a therapeutic agent;
   wherein the microspheres comprise a biodegradable portion and a non-biodegradable portion, wherein the biodegradable portion comprises the cyclodextrin, and wherein the microspheres retain a substantially spherical shape after degradation of the biodegradable portion when placed in a patient's body.

2. The microspheres of claim 1, wherein the cyclodextrin is functionalized to include a moiety that is polymerizable with said acrylamide monomer.

3. The microspheres of claim 1, wherein the cyclodextrin is selected from α(alpha)-cyclodextrin, β(beta)-cyclodextrin and γ(gamma)-cyclodextrin and combinations thereof.

4. The microspheres of claim 1, wherein the cyclodextrin is incorporated into the backbone of the polymer.

5. The microspheres of claim 1, wherein the polymeric material is cross-linked.

6. The microspheres of claim 1, wherein the copolymer comprises N-[tris(hydroxymethyl)methyl]acrylamide.

7. The microspheres of claim 1, wherein the microspheres are one or more of hydrophilic, swellable, and water insoluble.

8. The microspheres of claim 1, wherein the microspheres have an average diameter of from about 10 μm to about 2000 μm.

9. The microspheres of claim 1, wherein the therapeutic agent comprises a drug selected from one or more of the following: cisplatin, carboplatin, oxaliplatin, oxiplatin, satraplatin, picoplatin, nedaplatin, triplatin, lipoplatin, spiroplatin, iproplatin, docetaxel and paclitaxel.

10. The microspheres of claim 1, wherein the microspheres are configured to decrease the flux of blood flow across a region of the vasculature of the patient by 90% or more regardless of whether the biodegradable portion of the microsphere has been degraded.

11. The microspheres of claim 1, wherein the cyclodextrin is distributed in a substantially uniform manner throughout the microsphere.

12. The microspheres of claim 1, wherein the cyclodextrin is disposed only on an outer surface of the microspheres.

13. A method of embolization, comprising:
   administering to a patient microspheres comprising:
      a biocompatible, polymeric material comprising a copolymer comprising an acrylamide monomer, wherein the acrylamide monomer is selected from N-[tris(hydroxymethyl)methyl]acrylamide and N,N'-methylenebis(acrylamide), and a cyclodextrin; and
      a therapeutic agent, wherein the therapeutic agent comprises a platinum-based drug, a taxol, an anthracycline, or a campothecin,
      wherein the microspheres comprise a biodegradable portion and a non-biodegradable portion, wherein the microspheres retain a substantially spherical shape after degradation of the biodegradable portion when placed in a patient's body;
   occluding a blood vessel with the microspheres; and
   releasing the therapeutic agent.

14. The method of claim 13, wherein the copolymer comprises N-[tris(hydroxymethyl)methyl]acrylamide.

15. The method of claim 14, wherein the therapeutic agent is released by degradation of the cyclodextrin.

16. The method of claim 13, wherein the therapeutic agent comprises a platinum-based drug selected from one or more of the following: cisplatin, carboplatin, oxaliplatin, oxiplatin, satraplatin, picoplatin, nedaplatin, triplatin, lipoplatin, spiroplatin, and iproplatin.

17. A method of manufacturing microspheres, the method comprising:
   obtaining an aqueous solution comprising one or more acrylamide monomers selected from N-[tris(hydroxymethyl)methyl]acrylamide and N,N'-methylenebis(acrylamide), and an olefin-containing cyclodextrin;
   obtaining an oil;
   mixing the aqueous solution into the oil; and
   polymerizing the one or more acrylamide monomers and the olefin-containing cyclodextrin after the aqueous solution has been mixed into the oil; and
   isolating microspheres formed by the polymerization of the one or more acrylamide monomers and the olefin-containing cyclodextrin, wherein the microspheres comprise a biodegradable portion and a non-biodegradable portion, and wherein the microspheres are configured to retain a substantially spherical shape after degradation of the biodegradable portion when placed inside a patient's body.

18. The method of claim 13, wherein the cyclodextrin is functionalized to include a moiety that is polymerizable with said acrylamide monomer.

19. The method of claim 17, wherein the one or more one or more acrylamide monomers is N-[tris(hydroxymethyl)methyl]acrylamide.

* * * * *